(12) United States Patent
Ginsburg et al.

(10) Patent No.: US 9,901,428 B2
(45) Date of Patent: Feb. 27, 2018

(54) DENTAL DEVICES AND SYSTEMS AND METHODS FOR MAKING THE SAME

(71) Applicant: GOOD FIT TECHNOLOGIES, INC., Boston, MA (US)

(72) Inventors: Stephen Ginsburg, Wellesley, MA (US); Marc Ginsburg, New York, NY (US)

(73) Assignee: GOOD FIT TECHNOLOGIES, INC., Boston, MA (US)

( * ) Notice: Subject to any disclaimer, the term of this patent is extended or adjusted under 35 U.S.C. 154(b) by 46 days.

(21) Appl. No.: 13/842,788

(22) Filed: Mar. 15, 2013

(65) Prior Publication Data

US 2014/0272787 A1     Sep. 18, 2014

(51) Int. Cl.
| | |
|---|---|
| *A61C 3/08* | (2006.01) |
| *A61C 13/01* | (2006.01) |
| *A61C 13/00* | (2006.01) |
| *A61C 13/10* | (2006.01) |
| *A61C 13/20* | (2006.01) |

(52) U.S. Cl.
CPC .......... *A61C 13/04* (2013.01); *A61C 13/0004* (2013.01); *A61C 13/0022* (2013.01); *A61C 13/01* (2013.01); *A61C 13/1003* (2013.01); *A61C 13/20* (2013.01); *A61C 13/206* (2013.01)

(58) Field of Classification Search
CPC ..... A61C 13/01; A61C 13/04; A61C 13/1003; A61C 13/20; A61C 13/206; A61C 13/08; A61C 13/225; A61C 13/24
USPC ............................................... 433/171, 199.1
See application file for complete search history.

(56) References Cited

U.S. PATENT DOCUMENTS

| | | | |
|---|---|---|---|
| 3,762,848 A | 10/1973 | Muller | |
| 3,813,777 A * | 6/1974 | Van Handel et al. | ........ 433/171 |
| 4,175,322 A * | 11/1979 | Tureaud | ................. A61C 13/00 433/171 |
| 4,227,877 A | 10/1980 | Tureaud et al. | |

(Continued)

FOREIGN PATENT DOCUMENTS

| | | |
|---|---|---|
| AU | 483943 | 3/1976 |
| JP | 2008168065 | 7/2008 |
| WO | WO0027556 | 5/2000 |

OTHER PUBLICATIONS

International Search Report for PCT/US14/24579—filed Mar. 12, 2014. ISR dated Oct. 23, 2014.

(Continued)

*Primary Examiner* — Cris L Rodriguez
*Assistant Examiner* — Mirayda A Aponte
(74) *Attorney, Agent, or Firm* — Robert W. Morris; Ojeiku C. Aisiku; Eckert Seamans Cherin & Mellott, LLC

(57) ABSTRACT

Dental devices and systems and methods for making the same are provided. In at least one embodiment, a method for fabricating an arch-shaped device for coupling to a patient's mouth is provided. The method can include disposing each of a plurality of teeth into respective teeth receptors of an inlay device, positioning the inlay device in a recess of a lower portion of a mold device, and coupling the lower portion to an upper portion of the mold device to sandwich the inlay device therebetween. The method can also include injecting a base compound into an injection hole of the mold device, and processing the base compound to integrate the base compound with the plurality of teeth.

9 Claims, 20 Drawing Sheets

(56) References Cited

U.S. PATENT DOCUMENTS

| | | | |
|---|---|---|---|
| 4,361,528 A | | 11/1982 | Ginsburg et al. |
| 4,370,133 A | * | 1/1983 | Stempel .................. 433/171 |
| 4,413,979 A | | 11/1983 | Ginsburg et al. |
| 4,654,006 A | * | 3/1987 | Kusano et al. ............ 433/168.1 |
| 4,808,184 A | | 2/1989 | Tepic |
| 5,304,063 A | | 4/1994 | Ginsburg |
| 5,403,186 A | | 4/1995 | Ginsburg |
| 5,775,900 A | * | 7/1998 | Ginsburg ........... A61C 13/0001 433/171 |
| 2007/0190488 A1 | | 8/2007 | Rusler |
| 2008/0108007 A1 | | 5/2008 | Kong et al. |
| 2010/0297581 A1 | | 11/2010 | Wallace |
| 2012/0107771 A1 | * | 5/2012 | Hrenak ................ A61C 13/267 433/171 |

OTHER PUBLICATIONS

Dentistry Today, (Ginsberg, Stephen J. and Cavalier, Neil. A New Two-Appointment Custom Denture Technique. [online], Aug. 31, 2002, pp. 1-5, [retrieved on Jul. 31, 2014], retrieved from the Internet: http://www,dentistrytoday.com/prosthodontics/prosthetics/1729.

Glidewell Laboratories, Inclusive Screw-Retained Hybrid Denture [online], http://www.glidewelldental.com/lab/services/inclusive-screw-retained-denture.aspx, 2011, pp. 1 and 2, [retrieved on Jul. 31, 2014], retrieved from the Internet: http://web.archive.org/web/20111001035339/http://www.glidewelldental.com/lab/services/inclusive-screw-retained-denture.aspx.

Pritidenta, priti®process [online], http://www.pritidenta.com/cms/pritiprocess.html, 2013, pp. 1 and 2 [retrieved on Jul. 31, 2014], retrieved from the Internet: http://web.archive.org/web/20130225183443/http://www.pritidenta.com/cms/pritiprocess.html.

Miradent.com, Dental Thermoplastics for the Future [online], http://www.miradent.com/index.shtml, 2002, [retrieved on Jul. 31, 2014], retrieved from the Internet: http://web.archive.org/web/20020628124333/http://www.miradent.com/index.shtml.

Miradent.com, Miradent Products [online], http://www.miradent.com/products/, 2002, [retrieved on Jul. 31, 2014], retrieved from the Internet: http://web.archive.org/web/20020628125147/http://www.miradent.com/products/.

Miradent.com, The 1 Visit Miradent Denture (Product Instructions) [online], http://miradent.com/products/productinstructions196.shtml, 2002, pp. 1-5, [retrieved on Jul. 31, 2014], retrieved from the Internet: http://web.archive.org/web/20020628125259/http://www.miradent.com/products/productinstructions196.shtml.

Miradent.com, The 1 Visit Miradent Denture (Product Overview) [online], http://www.miradent.com/products/productoverview196.shtml, 2002, [retrieved on Jul. 31, 2014], retrieved from the Internet: http://web.archive.org/web/20020706084827/http://www.miradent.com/products/productoverview196.shtml.

Miradent.com, The C&B Tray (Product Instructions) [online], http://www.miradent.com/products/productinstructions197.shtml, 2002, pp. 1-3, [retrieved on Jul. 31, 2014], retrieved from the Internet: http://web. archive.org/web/20020714050500/http://www.miradent.com/products/productinstructions197.shtml (captured ).

Miradent.com, The C&B Tray (Product Overview) [online], http://www.miradent.com/products/productoverview197.shtml, 2002, [retrieved on Jul. 31, 2014], retrieved from the Internet: http://web.archive.org/web/20021007223937/http://www.miradent.com/products/productoverview197.shtml (captured ).

Miradent.com, The Denture Arch (Product Instructions) [online], http://www.miradent.com/products/productsinstructions231.shtml, 2002, pp. 1 and 2, [retrieved on Jul. 31, 2014], retrieved from the Internet: http://web.archive.org/web/20020628125332/http://www.miradent.com/products/productinstructions231.shtml (captured ).

Miradent.com, The Denture Arch (Product Overview) [online], http://www.miradent.com/products/productoverview231.shtml, 2002, [retrieved on Jul. 31, 2014], retrieved from the Internet: http://web.archive.org/web/20021007230707/http://www.miradent.com/products/productoverview231.shtml.

Miradent.com, The Denture Tray (Product Instructions) [online], http://www.miradent.com/products/productinstructions200.shtml, 2002, pp. 1-3, [retrieved on Jul. 31, 2014], retrieved from the Internet: http://web.archive.org/web/20020628125251/http://www.miradent.com/products/productinstructions200.shtml.

Miradent.com, The Denture Tray (Product Overview) [online], http://www.miradent.com/products/productoverview200.shtml, 2002, [retrieved on Jul. 31, 2014], retrieved from the Internet: http://web.archive.org/web/20020628130431/http://www.miradent.com/products/productoverview200.shtml.

Miradent.com, The Emergency Denture (Product Instructions) [online], http://www.miradent.com/products/productinstructions232.shtml, 2002, [retrieved on Jul. 31, 2014], retrieved from the Internet: http://web.archive.org/web/20021020140119/http://www.miradent.com/products/productinstructions232.shtml.

Miradent.com, The Emergency Denture (Product Overview) [online], http://www.miradent.com/products/productoverview232.shtml, 2002, [retrieved on Jul. 31, 2014], retrieved from the Internet: http://web.archive.org/web/20021212053820/http://www.miradent.com/products/productoverview232.shtml.

Miradent.com, The Implant Insta Stent & Surgical Guide (Product Instructions) [online], http://www.miradent.com/products/productinstructions198.shtml, 2002, pp. 1-3, [retrieved on Jul. 31, 2014], retrieved from the Internet: http://web.archive.org/web/20020628125257/http://www.miradent.com/products/productinstructions198.shtml.

Miradent.com, The Implant Insta Stent & Surgical Guide Overview [online], http://www.miradent.com/products/productoverview198.shtml, 2002, [retrieved on Jul. 31, 2014], retrieved from the Internet: http://web:archive.org/web/20020628130304/http://www.miradent.com/products/productoverview198.shtml.

Miradent.com, The Interim Denture (Product Instructions) [online], http://www.miradent.com/products/productinstructions199.shtml, 2002, [retrieved on Jul. 31, 2014], retrieved from the Internet: http://web.archive.org/web/20020628125218/http://www.miradent.com/products/productinstructions199.shtml.

Miradent.com, The Interim Denture (Product Overview) [online], http://www.miradent.com/products/productoverview199.shtml, 2002, [retrieved on Jul. 31, 2014], retrieved from the Internet: http://web.archive.org/web/20020628130521/http://www.miradent.com/products/prod uctoverview199.shtml.

Miradent.com, The Vanity Denture (Product Instructions) [online], http://www.miradent.com/products/productinstructions201.shtml, 2002, [retrieved on Jul. 31, 2014], retrieved from the Internet: http://web.archive.org/web/20021221133938/http://www.miradent.com/products/productinstructions201.shtml.

Miradent.com, The Vanity Denture (Product Overview) [online], http://www.miradent.com/products/productoverview201.shtml, 2002, [retrieved on Jul. 31, 2014], retrieved from the Internet: http://web.archive.org/web/20021007224513/http://www.miradent.com/products/productoverview201.shtml.

Miradent.com, Miradent Technology [online], http://www:miradent.com/technology/, 2002, [retrieved on Jul. 31, 2014], retrieved from the Internet: http://web.archive.org/web/20020628130607/http://www.miradent.com/technology/.

Miradent.com, The Denture Form—How It Works [online], http://miradent.com/products-dentureform.shtml, 2007, pp. 1-3 [retrieved on Jul. 31, 2014], retrieved from the Internet: http://web.archive.org/web/20070430170333/http://miradent.com/products-dentureform.shtml (captured ).

AvaDent, Products [online], 2013, pp. 1-7, [retrieved on Jul. 31, 2014], retrieved from the Internet: http://web.archive.org/web/20130608184533/http://www.avadent.com/professional/solutions/.

AvaDent, Getting Started with AvaDent Kit [online], prior to Mar. 6, 2013, pp. 1-3, [retrieved on Jul. 31, 2014], retrieved from the Internet: https:/store.avadent.com/Getting-started-with-AvaDent-kit.html.

AvaDent, Computer precision fit [online], 2013, pp. 1-3, [retrieved on Jul. 31, 2014], retrieved from the Internet: http://web.archive.org/web/20130608184533/http://www.avadent.com/professional/solutions/.

(56) References Cited

OTHER PUBLICATIONS

Dentca.com, http://dentca.com/, 2012, pp. 1 and 2 [retrieved on Jul. 31, 2014], retrieved from the Internet: http://web.archive.org/web/20120225051951/http://dentca.com.

Dentca.com, About DENTCA [online], http://www.dentca.com/aboutUs.asp, 2012, pp. 1 and 2, [retrieved on Jul. 31, 2014], retrieved from the Internet: http://web.archive.org/web/20120618144630/http://www.dentca.com/aboutUs.asp.

Envisiontec.de, the benchmark in 3D printing [online], http://www.envisiontec.de/, 2013, pp. 1 and 2, [retrieved on Jul. 31, 2014], retrieved from the Internet: http://web.archive.org/web/20130306062409/http://www.envisiontec.de/ (captured Mar. 6, 2013).

Envisiontec.com, Dental [online], http://envisiontec.com/applications/dental, 2013, pp. 1 and 2, [retrieved on Jul. 31, 2014], retrieved from the Internet: http://web.archive.org/web/20130316071646/http://envisiontec.com/applications/dental/.

Envisiontec, Octoflash [online], Dec. 2012, [retrieved on Jul. 31, 2014], retrieved from Internet: http://envisiontec.com/envisiontec/wp-content/uploads/2012/12/Machine-Otoflash.pdf.

Envisiontec, PixCera [online], Dec. 2012, [retrieved on Jul. 31, 2014], retrieved from Internet: http://envisiontec.com/envisiontec/wp-content/uploads/2012/12/Machine-PixCera.pdf.

Envisiontec, 3DENT [online], Dec. 2012, [retrieved on Jul. 31, 2014], retrieved from Internet: http://envisiontec.com/envisiontec/wp-content/uploads/2013/02/MK-MCS-3Dent-V01-FN-EN.pdf.

Envisiontec, Brochure [online], Dec. 2012, [retrieved on Jul. 31, 2014], Retrieved from Internet: http://envisiontec.com/envisiontec/wp-content/uploads/2012/12/MK-NOA-DentalBrochure-V01-FNF-EN.pdf.

\* cited by examiner

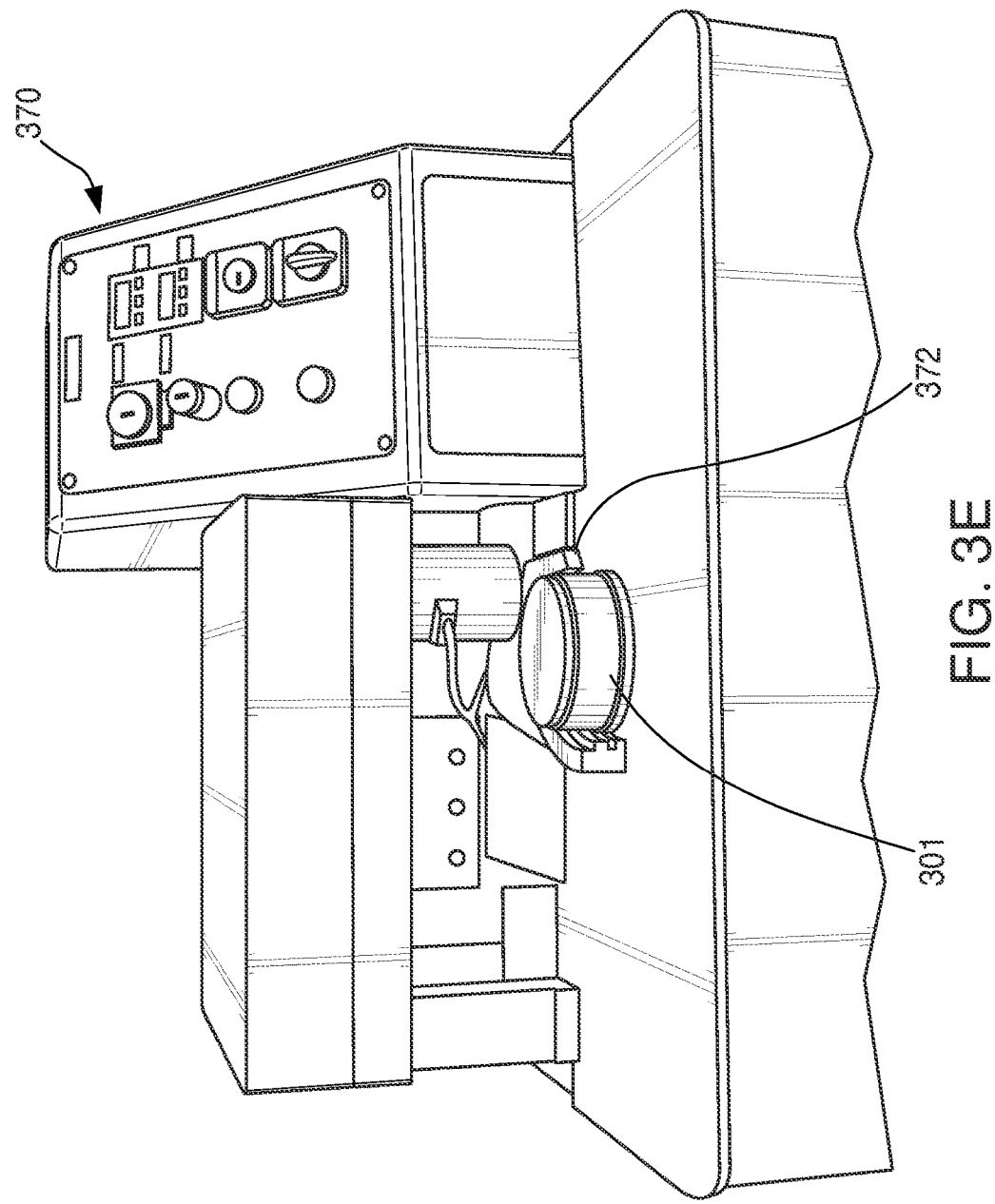

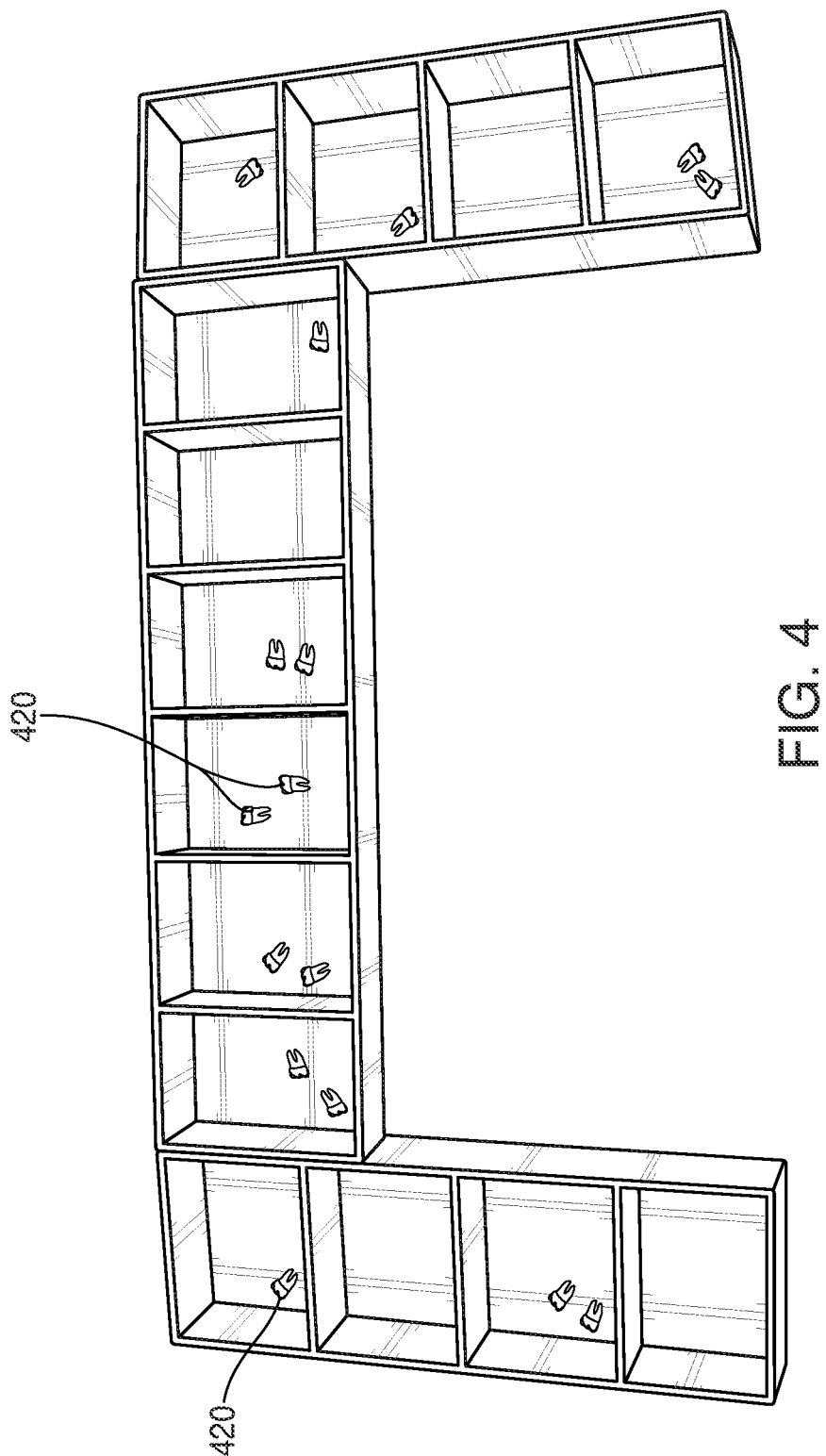

DENTAL DEVICES AND SYSTEMS AND METHODS FOR MAKING THE SAME

FIELD OF THE INVENTION

This relates to dental devices and systems and methods for making the same.

BACKGROUND OF THE INVENTION

The loss of one's teeth is one of the biggest health issues in the world today—millions of people are affected by this condition. Moreover, as people continue to live longer, this condition will continue to grow and more and more people will rely on dentures to replace some or all of their teeth as they age. Dentures, however, can be embarrassing for some people to wear. Many elderly people, for example, rely on dentures to carry out many of their daily activities. For instance, not only can dentures provide one with the ability to chew and enjoy a good meal, they can also help people speak properly, as well as put on a confident smile.

Although dentures provide many advantages to a patient, the patient may be required to visit their dental practitioner (e.g., a prosthodontist) multiple times and the practitioner may also have to rely upon an equal number of laboratory procedures (which can include things such as individually setting teeth in wax forms based on data provided by a dentist, which can be time consuming and labor intensive) before the dentist can obtain a suitable set of dentures with the right look, feel, and fit. At each visit, the practitioner may send an interim denture back to a denture manufacturer for any adjustments that might need to be made, which can require the manual labor of highly skilled technicians. Because of this, denture fabrication appears to be more of an art than a science—a particular adjustment to a denture, performed by a given technician on a given day, may be different than the same adjustment by the same technician on a different day. Any slight error in the placement of one or more teeth in a denture (e.g., a lower or mandibular denture) may render it incompatible with a counterpart denture (e.g., an upper or maxillary denture). This error-prone and inefficient process of fine tuning a denture increases dental costs, and can frustrate both the practitioner and the patient. Thus, there is a need for improved dental devices and systems and methods for the same.

SUMMARY OF THE INVENTION

This relates to dental devices and systems and methods for making the same. It is an object to make it easier and more efficient for dental practitioners, patients, and dental device laboratories to arrive at one or more suitable dental devices (e.g., dentures) for the patient in as few as a single patient visit, which can be more economical and efficient than conventional dental procedures and techniques. Moreover, it is an object to make dentures that are produced in a more consistent manner over time, such that an otherwise "identical" set of dentures produced one month should be substantially similar to another set of "identical" dentures produced later in time.

In at least one embodiment, a dental arch device is provided. The arch device can be similar to an upper denture, and can correspond and fit to an upper portion of a patient's mouth, such as an upper or maxillary jaw. Alternatively, the arch device can be similar to a lower denture, and can correspond and fit to a lower portion of a patient's mouth, such as a lower or mandibular jaw. For example, an arch device can be constructed to fit to a corresponding one of a patient's upper (or maxillary) and lower (or mandibular) teeth and gum portions. The arch device can serve as at least a partial replacement one or more teeth of that portion. The arch device can be composed of one or more materials or compounds that are compatible with a patient's mouth. More particularly, the compounds can be chemically compatible with the inside of a patient's mouth. For example, the compounds can include polymethyl methacrylate ("PMMA") thermoplastic.

The arch device can be smaller than a full or conventional denture. A typical denture includes a set of teeth coupled to a uniform base material. The uniform base material includes a lingual section (e.g., the curved teeth retaining portion of the denture facing a tongue or oral cavity) coupled to the teeth, and a framework or flange section that provides overall structural integrity to the denture and that extends from the lingual section to a border of the denture. When the arch device is used to fabricate a denture, base material can be added to the base of the arch device to form a flange for the resulting denture. In this manner, the arch device can constitute a lingual portion of the denture that is integrated to a distinct flange portion.

The arch device can be employed during a patient's fitting session. For example, the arch device can be inserted and coupled to a corresponding portion of the patient's mouth. It can often be the case, however, that even when an arch device is suitably sized for a patient, the arch device may not fit precisely or comfortably in the patient's mouth. Thus, in at least one embodiment, the arch device can be adjustable. More particularly, the arch device can be constructed from one or more materials that allow the arch device to be pliable or flexible. The arch device may not always be adjustable, however. Rather, the arch device may only be adjustable when subjected to certain temperatures. For example, the arch device may only be adjustable when heated above certain temperatures. Thus, during a patient visit, if a particular arch device selected by a dental practitioner appears to be insertable into the patient's mouth, but may need certain minor adjustments, there would be no need to send the arch device to a dental device manufacture for any adjustments. Rather, the practitioner can simply heat the arch device to at least a predefined temperature, and can make the necessary adjustments to the arch device on the spot. For example, the arch device can be subjected to heat for a few minutes, and then it can be adjusted to the shape needed for a comfortable fit, and then can be re-inserted into the patient's mouth to check the fit. This adjustment process can be repeated until the arch device fits properly and comfortably in the patient's mouth.

In at least one embodiment, a pair of arch devices is provided. The arch devices can be a match, and can include an upper or maxillary device that is similar to an upper denture, and a corresponding lower or mandibular device that is similar to a lower denture.

In at least one embodiment, a kit of dental arch devices is provided. The kit can include variably sized pairs of counterpart or matching arch devices. Each pair may include an upper or maxillary arch device and a lower or mandibular arch device, and one pair can be larger than another pair. In these embodiments, a practitioner can select one or more of the pairs of arch devices from the kit during a denture fitting session. For example, a first pair can be selected and inserted in a patient's mouth (e.g., one arch device at a time or both arch devices simultaneously). If the selected arch devices are too large or too small for the particular patient, a pair having a different size can be selected, and the fitting can be repeated until a suitable pair is identified. Any adjustments that may be required to each arch device of the pair can be made in the manner described above.

In at least one embodiment, an arch device fabrication apparatus can be provided. The apparatus can include a mold device having separable upper and lower portions. The mold device can be composed of metal (e.g., brass beryllium, etc.), and can include specific structural features, and can be sized and shaped to produce one or more arch devices. In at least one embodiment, the mold device can be manufactured from a master arch device that may be created from a master denture. For example, the mold device can be constructed from one or more master dentures that have certain portions (e.g., some or all of its base material) removed so as to form a suitably sized and shaped arch device.

In at least one embodiment, a base compound can be employed in the manufacture of an arch device. The base compound can have specific chemical properties that allow a completed arch device to behave in a certain manner when subjected to heat. For example, the base compound can have properties that allow a completed arch device to be adjustable in shape when subjected to sufficient heat. In general, it can be advantageous to have the "sufficient" heat be at a level not normally accessible by a patient in order to prevent the patient from changing the fit inadvertently.

In at least one embodiment, the base compound can include a mixture of polymer and monomer. The base compound can be formed by mixing predefined amounts of polymer with a corresponding amount of monomer, and can be cooled or frozen to form a dough-like substance suitable for fabricating an arch device.

In at least another embodiment, the arch device fabrication apparatus can also include an inlay device. The inlay device can be a curve-shaped tray configured to retain a set of teeth during manufacture of the arch device. The inlay device can be composed of any suitable material (e.g., silicone), and can be sized and shaped similar to an arch device to be manufactured. The inlay device can also include multiple recesses for receiving the set of teeth during production of the arch device.

The inlay device can be constructed using any suitable process. In at least one embodiment, the inlay device can be manufactured by using a master arch device (e.g., similar to the master arch device described above) and a mold device (e.g., similar to the mold device described above). More particularly, a master arch device can be at least partially enclosed by upper and lower portions of the mold device, and an inlay compound can be injected into the mold device to fill vacant areas within the mold device and around the master arch device. In this manner, the inlay device can be employed to manufacture an arch device that can have similar physical characteristics of the master arch device used to create that inlay device. The inlay compound can, for example, include one or more types of silicone. In at least one embodiment, the inlay device can also include one or more types of epoxy.

Other dental devices similar to an arch device are also provided. For example, in at least one embodiment, a denture form device can be provided. The denture form device can resemble a denture, but can be composed of material that allows the denture form device to be adjustable. In at least one embodiment, a fabrication apparatus, similar to the fabrication apparatus for an arch device, is also provided for fabricating a denture form device.

Moreover, various techniques for fabricating dentures are provided in various embodiments. For example, dentures can be fabricated by leveraging one or more of an arch device and a denture form device, in conjunction with one or more of computer-aided design ("CAD"), computer-aided manufacturing ("CAM"), three-dimensional (3D) printing, and the like.

In at least one embodiment, a denture is provided. The denture can include an arch-shaped lingual portion. The lingual portion can include a base and a plurality of teeth disposed on the base. The denture can also include a distinct flange portion, the flange portion being integrated to the base.

In at least one embodiment, an arch device for coupling to a jaw is provided. The arch device can include an arch-shaped base and a plurality of teeth disposed on the base. A shape and fit of the arch device can be adjustable when the arch device is subjected to a predefined temperature.

In at least one embodiment, a kit for use in providing at least one suitable denture for a patient's mouth is provided. The kit can include a first pair of upper and lower arch devices. The kit can also include at least a second pair of upper and lower arch devices. Each of the first pair and the at least a second pair of arch devices can be configured to fit to corresponding portions of a patient's mouth. A size of the upper and lower arch devices of the first pair can be different from a size of the upper and lower arch devices of the at least a second pair. A shape of each of the upper and lower arch devices of the first and the at least a second pair can be adjustable when that device is subjected to a predefined amount of heat.

In at least one embodiment, a partial arch device is provided. The partial arch device can include a base and a plurality of teeth positioned along the base. The base can include at least one groove disposed adjacent at least one tooth of the plurality of teeth. The at least one groove can configured to receive at least one tooth in a patient's mouth. The partial arch device can be adjustable in shape when the partial arch device is subjected to a predefined temperature.

In at least one embodiment, an inlay device for use in fabricating an arch device is provided. The inlay device can include a curved tray. The tray can include a recess that spans from one end of the tray to another end of the tray. The recess can have a plurality of teeth receptors each configured to receive a respective tooth of a plurality of teeth. The inlay device can also include at least one ear coupled to the curved tray. The at least one ear can be configured to couple to at least one ear receptor of a mold device.

In at least one embodiment, a mold device for fabricating an arch device is provided. The mold device can include a lower portion having a first arch-shaped recess and a first injection slot, and an upper portion having a second arch-shaped recess and a second injection slot. The first and second injection slots can form an injection hole when the lower and upper portions are combined. The first recess can be configured to receive an inlay device, and the second recess can be configured to receive a base compound injected through the injection hole.

In at least one embodiment, a method for fabricating an arch-shaped device for coupling to a patient's mouth is provided. The method can include disposing each of a plurality of teeth into respective teeth receptors of an inlay device, positioning the inlay device in a recess of a lower portion of a mold device, and coupling the lower portion to an upper portion of the mold device to sandwich the inlay device therebetween. The method can also include injecting a base compound into an injection hole of the mold device, and processing the base compound to integrate the base compound with the plurality of teeth.

In at least one embodiment, a method of fabricating a base compound operative to form a base of an arch device is provided. The method can include mixing a plurality of materials together. The materials can be mixed in a predefined ratio. The mixture can exhibit properties suitable for bonding to a plurality of teeth during fabrication of the arch device. The method can also include processing the mixture to provide the base compound.

In at least one embodiment, a method of fabricating an inlay compound operative to form an inlay device for a mold is provided. The method can include mixing a plurality of materials together. The materials can be mixed in a predefined ratio. The mixture can exhibit properties for retaining a plurality of teeth during fabrication of an arch device. The method can also include curing the mixture at a predefined temperature to provide the inlay compound.

In at least one embodiment, a method of fabricating an inlay device for a mold device is provided. The method can include disposing a master arch device on an upper portion of the mold device, and coupling the upper portion to a lower portion of the mold device to sandwich the master arch device therebetween. An injection slot of the upper portion and an injection slot of the lower portion can form an injection hole of the mold device when the upper and lower portions are coupled together. The method can also include injecting an inlay compound into the injection hole and processing the injected compound to provide the inlay device.

In at least one embodiment, a denture form device is provided. The denture form device can include a unitary structure having a base portion and a flange portion, and a plurality of teeth integrated with the base portion. The denture form device can be adjustable when the denture form device is subjected to heat.

BRIEF DESCRIPTION OF THE DRAWINGS

The above and other features of the present invention, its nature and various advantages will be more apparent upon consideration of the following detailed description, taken in conjunction with the accompanying drawings in which:

FIG. 3E shows a front perspective view of a polymerization press coupled to the mold device of FIGS. 3A and 3B, in accordance with at least one embodiment;

FIG. 4 shows a top view of a set of teeth disposed in a tray, in accordance with at least one embodiment;

DETAILED DESCRIPTION OF THE PREFERRED EMBODIMENTS

Figure 1:
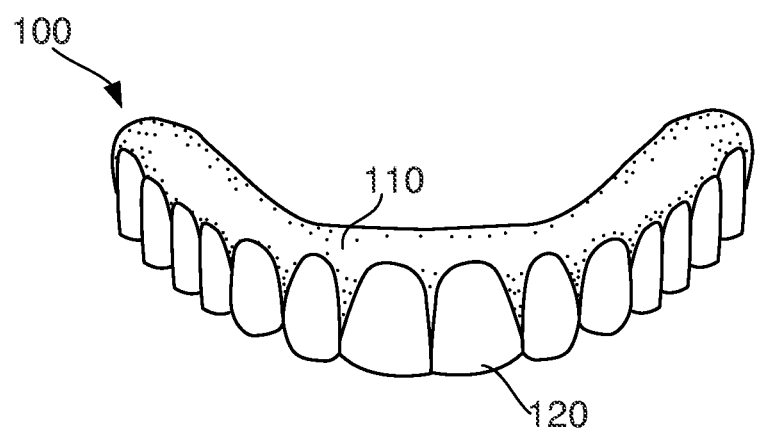
FIG. 1 shows a front perspective view of an arch device configured to fit to a maxillary portion of a patient's mouth, in accordance with at least one embodiment.
Figure 2:
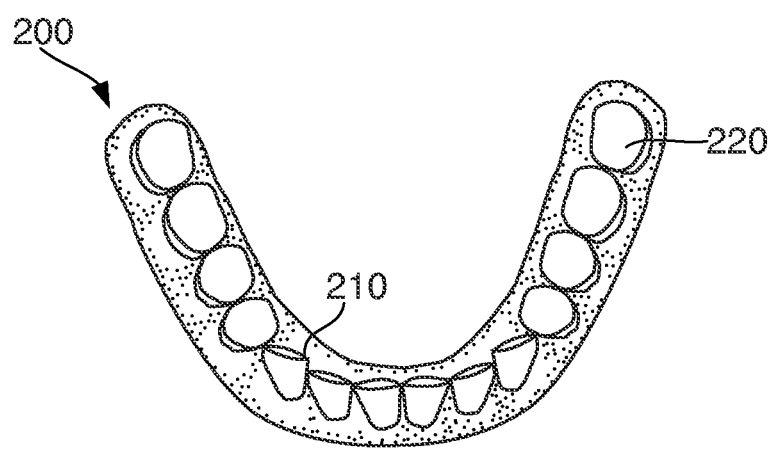
FIG. 2 is a top view of an arch device configured to fit to a mandibular portion of a patient's mouth, in accordance with at least one embodiment.

FIG. 1 shows a front perspective view of an arch device 100 configured to fit to a maxillary portion of a patient's mouth. FIG. 2 is a top view of an arch device 200 configured to fit to a mandibular portion of a patient's mouth. As shown in FIG. 1, arch device 100 can include an arch-shaped or curved base 110 and a set of teeth 120 disposed on base 110 in a predefined order. Similarly, arch device 200 can include an arch-shaped base 210 and a set of teeth 220 disposed on base 210 in a predefined order. For the sake of brevity, the following description is only made for arch device 100. However, it should be appreciated that a similar description can be made for arch device 200.

Teeth 120 can be similar to teeth that one may have at an upper or maxillary portion of his mouth, or a lower or mandibular portion of his mouth. Each one of teeth 120 can be a standard tooth provided by a teeth or denture laboratory. For example, teeth 120 can be prefabricated, and can come in various shapes, sizes, and colors. As such, there may be thousands of teeth to choose from, with each tooth being constructed to occupy a predetermined location of a denture, for example. Moreover, each of teeth 120 can correspond to a specific position on a particular denture. For example, teeth identified or labeled as N13 and IN2 for an F type denture (not shown) can correspond to specific locations on a particular type of upper denture.

As shown in FIG. 1, teeth 120 can be disposed in a predefined manner on one side of base 110. Accordingly, arch device 100 can resemble teeth on a portion of a patient's gum. Arch device 100 can be composed of any suitable material. For example, arch device 100 can be composed of acrylic thermoplastic. This material can provide arch device 100 with the ability to change shape or adjust when arch device 100 is subjected to at least a predefined temperature.

Arch 100 can be employed as part of a patient's denture fitting session. In at least one embodiment, arch 100 can be included as part of a kit or set of arch devices (not shown). This kit can include, for example, variably sized pairs of matching upper or maxillary and lower or mandibular arch devices. During a fitting session, for example, one or more arch devices can be selected from the kit for a patient to try on. If a selected arch device is too large for the patient's mouth, for example, a smaller arch device can be selected.

When a suitably sized arch device is identified, it may generally fit in a corresponding portion of the patient's mouth, but may not necessarily fit precisely and comfortably in the mouth. In these instances, the identified arch device can be subjected to at least a predetermined temperature, which may cause the arch device to be pliable or flexible. That is, the arch device can become adjustable for a short period of time (which is related to the heating).

In at least one embodiment, the arch device can change from a rigid state to an adjustable state while positioned in a patient's mouth. In these embodiments, the arch device can be composed of material that allows it to become adjustable when subjected to a predefined range of temperatures (e.g., when subjected to a warm fluid that is not high enough to damage intra-oral tissue, such as 100° F. to 130° F.). In at least another embodiment, the adjustability of the arch device can be limited to a higher range of temperatures (e.g., between 130° F. and at least 212° F.), and thus, may need to be adjusted outside of a patient's mouth (e.g., by a dental practitioner or in a laboratory, which can require an additional patient visit after the laboratory processing session). In these embodiments, the arch device can be composed of slightly different materials or compounds. Regardless of what temperature is required to change the arch device to the adjustable state, the adjusted arch device can be left to cool for a predefined time, and the adjustment process can be repeated until the arch device fits precisely and comfortably in a corresponding portion of the patient's mouth.

When both an upper (or maxillary) and a lower (or mandibular) arch device are required, any adjustments made to an upper or lower arch device may require corresponding adjustments to the other arch device, and each of the upper and lower arch devices can be continually adjusted until they interact with each other properly inside the patient's mouth. Typically, a patient's upper and lower teeth position can be governed by the patient's mandibular or lower jaw. Thus, it can be preferable to make suitable adjustments to the lower arch first, and then make corresponding adjustments to the upper arch device (e.g., such that teeth of the upper arch device can properly align with those of the lower arch device).

In at least one embodiment, each arch device can be further processed to form a complete set of dentures for the patient. For example, a base material (e.g., wax or acrylic portion) can be added to each arch device (e.g., to base 110) to form a complete denture that includes a lingual portion and a distinct flange portion. This step can be performed either directly by a dental practitioner during a patient visit, or by a laboratory technician. If it is performed by the latter, the patient can be required to make at least another visit after the laboratory procedure.

In at least one embodiment, a pair of upper and lower arch devices (e.g., arch devices 100 and 200) can be provided over-the-counter (e.g., at a pharmacy) to a patient or customer as a measuring device for fabricating an emergency denture. The patient can adjust the over-the-counter arch devices (e.g., by subjecting the arch devices to warm or hot water as described above) until the arch devices fit and interact with one another or the patient's opposing, existing teeth or dentures properly. If desired, the patient can send the adjusted arch devices, which can serve as measuring devices, to a denture laboratory to create a complete set of replacement dentures.

Patients having dental implants installed during a visit often are often provided a temporary partial or full denture to bring home, since a permanent denture can often take months (e.g., four to six months) to fabricate. The temporary denture is often prepared in an advance for the patient, and may require the patient to have made multiple prior visits to fabricate. Thus, in at least one embodiment, an arch device is provided for fabrication of a temporary, emergency/spare, or long-term implant denture.

In at least another embodiment, the base of an arch device, suitable for use as an implant denture, can be similar to any one of arch devices 100 and 200, and can include a base coupled to a set of teeth. However, the base can have a unique form that is distinct from a base of an arch device (e.g., base 110 of arch device 100) that may be used in non-implant dentures. That is, the structural features of at least the base of an implant arch device can be optimized for use as an implant supported prosthesis. For example, the base of a modified arch device can include one or more recesses, dimples, or the like for interfacing with a patient's implants.

Figure 17:
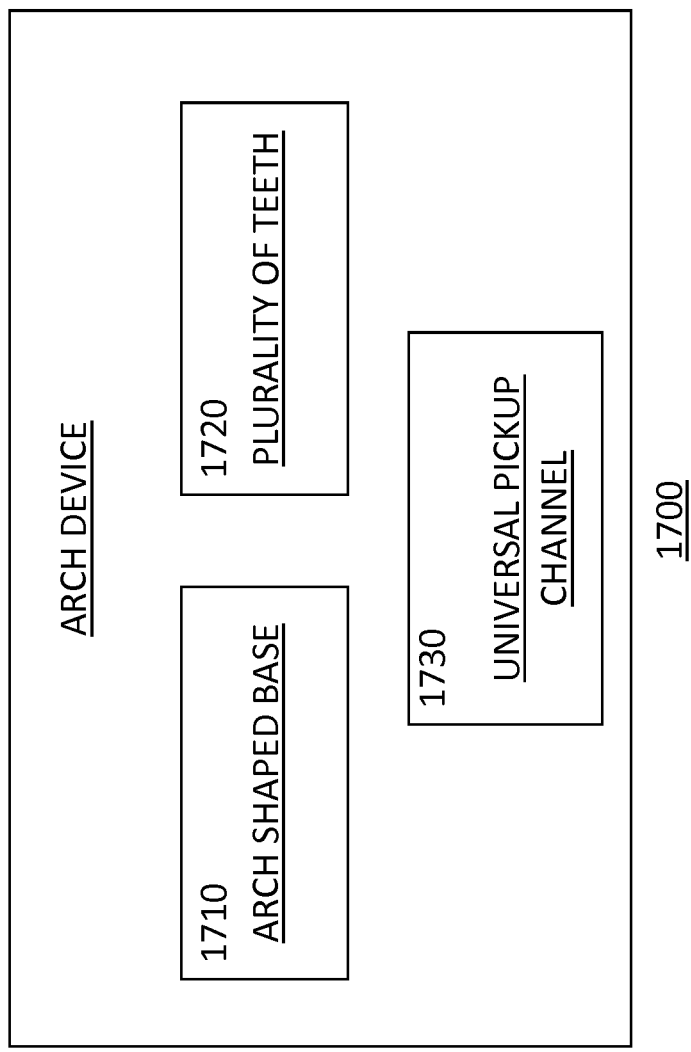
FIG. 17 is an illustrative block drawings of an arch device in accordance with at least one embodiment.

In at least another embodiment, as shown, for example, in FIG. 17, an arch device 1700, suitable for use as an implant denture, can include a universal pickup channel 1730 along a portion of its base 1710. This channel 1730 can be molded into the base 1710 as either a series of recesses or a single long recess, and can be configured to dispose along a patient's gum line such that the series of recesses (or single long recess) reside on any dental implants (e.g., metal screw, etc.) already embedded in the patient's gums. The channel can be cold cured (e.g., with acrylic) to anchor, polymerize, or otherwise couple, to the implanted material. When the implant finally fuses with the patient's bone (e.g., after a few months), the modified arch device can be further adjusted, if needed.

An arch device having a uniquely formed base or a pickup channel, as described above, can also be reinforced to maintain its structural integrity. For example, the arch device can be coated, or otherwise integrated, with a reinforcing material or agent (e.g., a Teflon strip). The arch device can be coated with this reinforcing material at any suitable point during or after fabrication of the arch device.

In at least one embodiment, an arch device having a universal pickup channel can be fabricated using a mold device similar to mold device 301. However, a recess of an upper portion of the mold device can include a ridge or protruding feature that forms the universal pickup channel in the base of the arch device (e.g., where base compound, such as base compound 359, can flow about or around the ridge, and when cured, results in a universal pickup channel of the resulting arch device). The ridge can also receive a reinforcing agent (e.g., Teflon strip) described above for reinforcing the arch device when fabricated. A fabrication process for an arch device having a universal pickup channel can thus be similar to process 800, but may also include disposing at least one reinforcing agent adjacent, along, or onto a ridge of a recess of an upper portion of a mold device (e.g., prior to injecting the base compound) such that a resulting arch device can be reinforced with a reinforcing agent, and include a pickup channel.

In at least another embodiment, an arch device may not include a unique form or a pickup channel as described above. Rather, a practitioner may drill, or otherwise form, one or more pickup channels along the base of the arch device, as needed, depending on the number of implants that need to be accommodated by the arch device.

Figure 18:
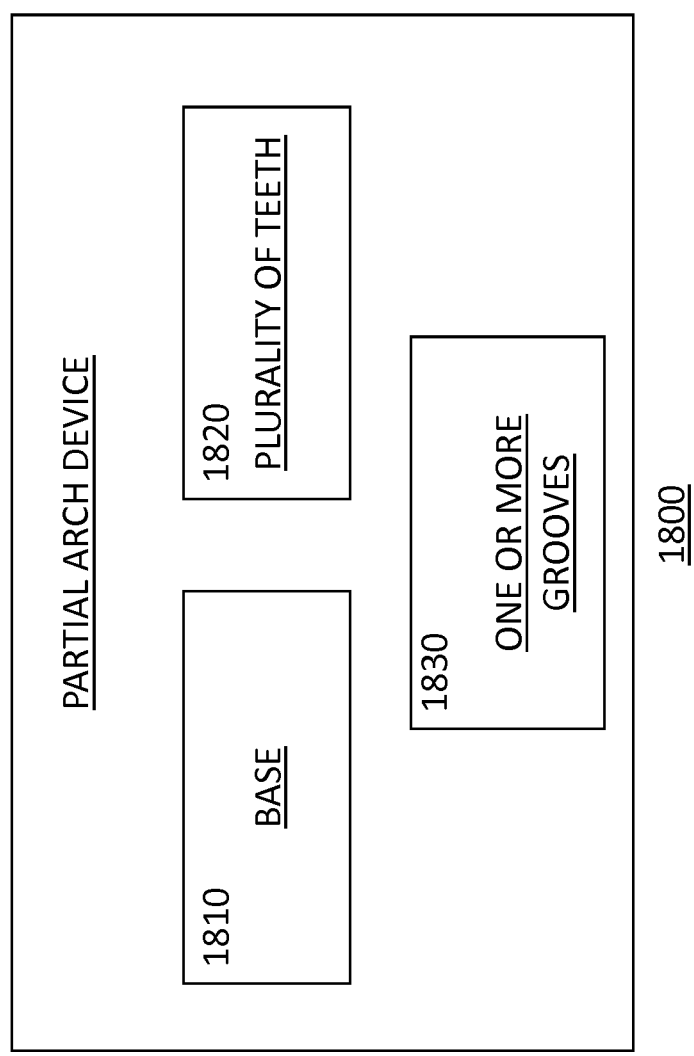
FIG. 18 is an illustrative block drawings of a partial arch device in accordance with at least one embodiment.

Some patients may have existing teeth, but may require a "flipper" device or a bridge to substitute for one or more missing teeth. Thus, in at least one embodiment, such as, for example, the embodiment shown in FIG. 18, an arch device can be similarly modified to form a partial arch device 1800. In these embodiments, select portions of a complete arch device can be trimmed or cut to form one or more grooves 1830 for receiving a patient's existing teeth. The modified arch device can then only include teeth 1820 that correspond to the patient's missing teeth. As with a complete arch device, the modified arch device can also be adjusted (e.g., as described above) to fit in the patient's mouth and function as an instant flipper or bridge. Any cut portions of the modified arch device can also be cold cured (e.g., with acrylic) to smoothen any sharp edges or surfaces. In at least one embodiment, when the modified arch device is used to provide a bridge for a patient, one or more implants or abutments can be prepared, and the corresponding teeth of the modified arch device can be fitted to the implants or abutments (e.g., similar to how the above-described universal pickup channel of the modified arch device can be integrated with dental implants).

Referring now to FIGS. 3A-3F, an arch device fabrication apparatus can include a mold device 301 having a lower portion 310 that is separable from an upper portion 320. The apparatus can also include an inlay device 330, and a base compound supplying device 340 for supplying or injecting a base compound 359 into mold device 301. The apparatus can also include at least one base compound container 350 for storing base compound 359 and for providing base compound 359 to supplying device 340.

Figure 3A:
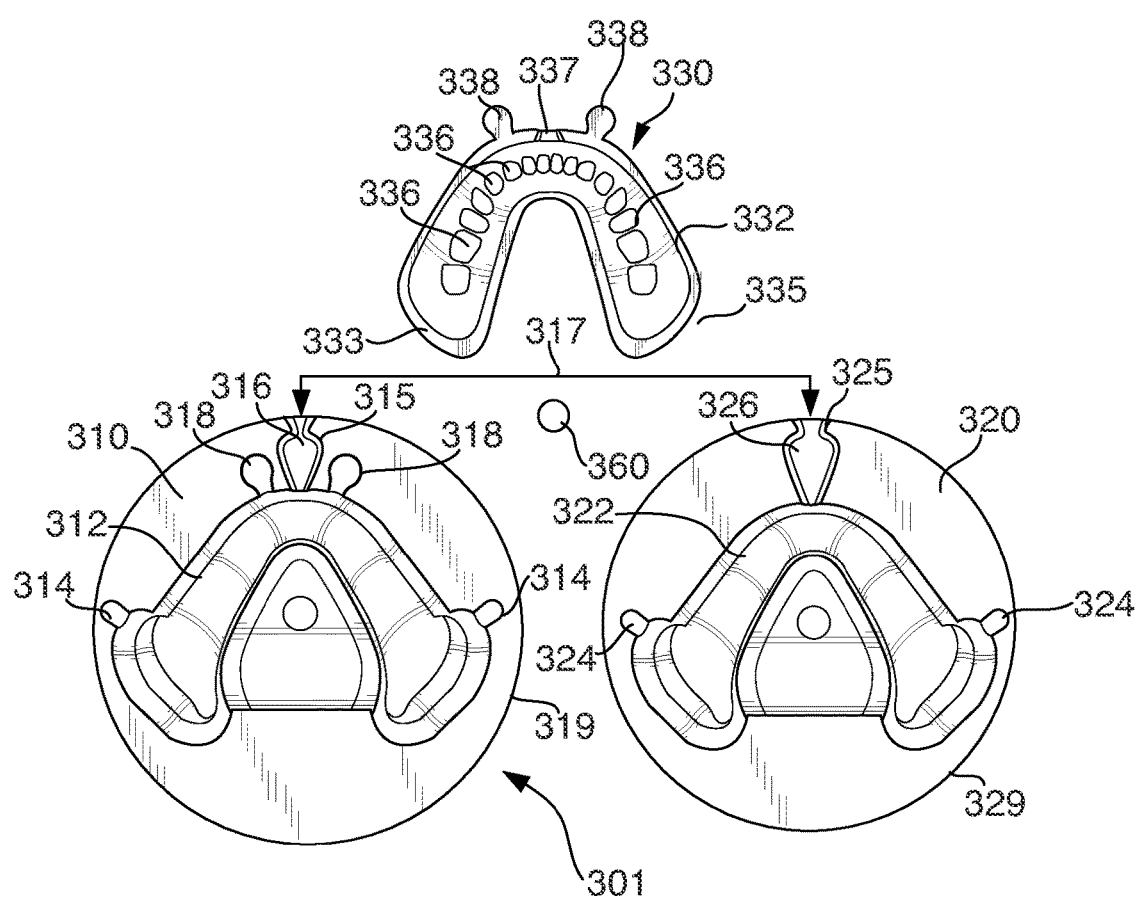
FIG. 3A shows top views of lower and upper portions of a mold device and an inlay device of an arch device fabrication apparatus for fabricating an arch device, in accordance with at least one embodiment.
Figure 3B:
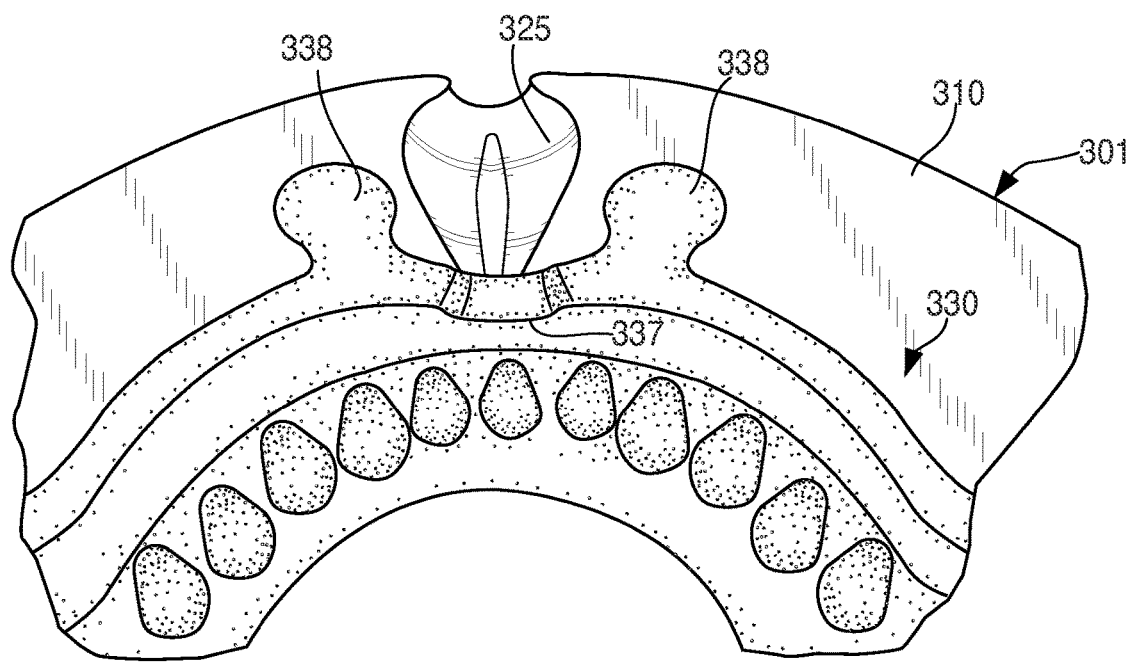
FIG. 3B shows a partial top view of the lower portion of the mold device of FIG. 3A and of the inlay device of FIG. 3A, in accordance with at least one embodiment.
Figure 3C:
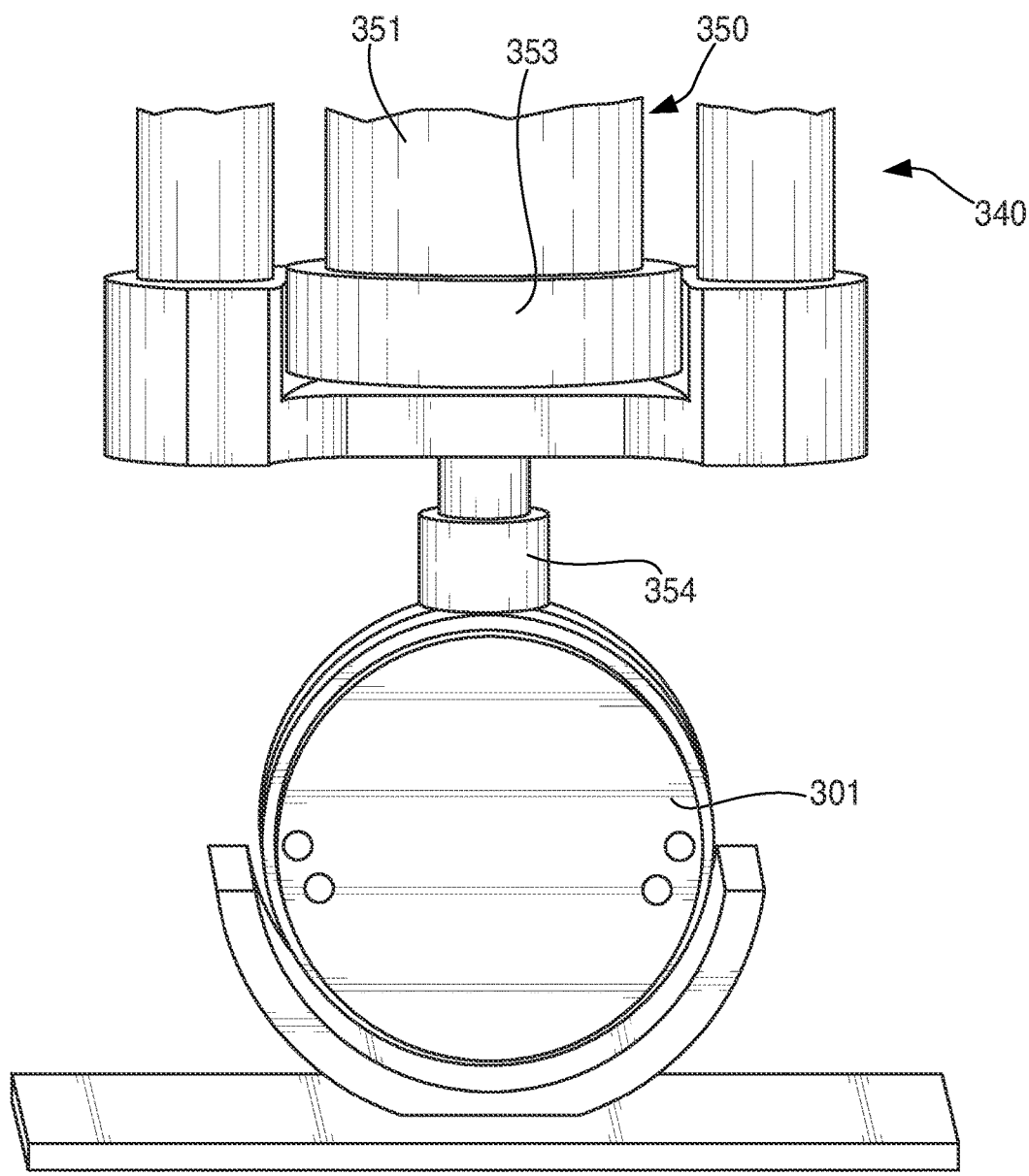
FIG. 3C shows a front view of a base compound supplying device coupled to the mold device of FIGS. 3A and 3B, and coupled to a base compound container, in accordance with at least one embodiment.
Figure 3D:
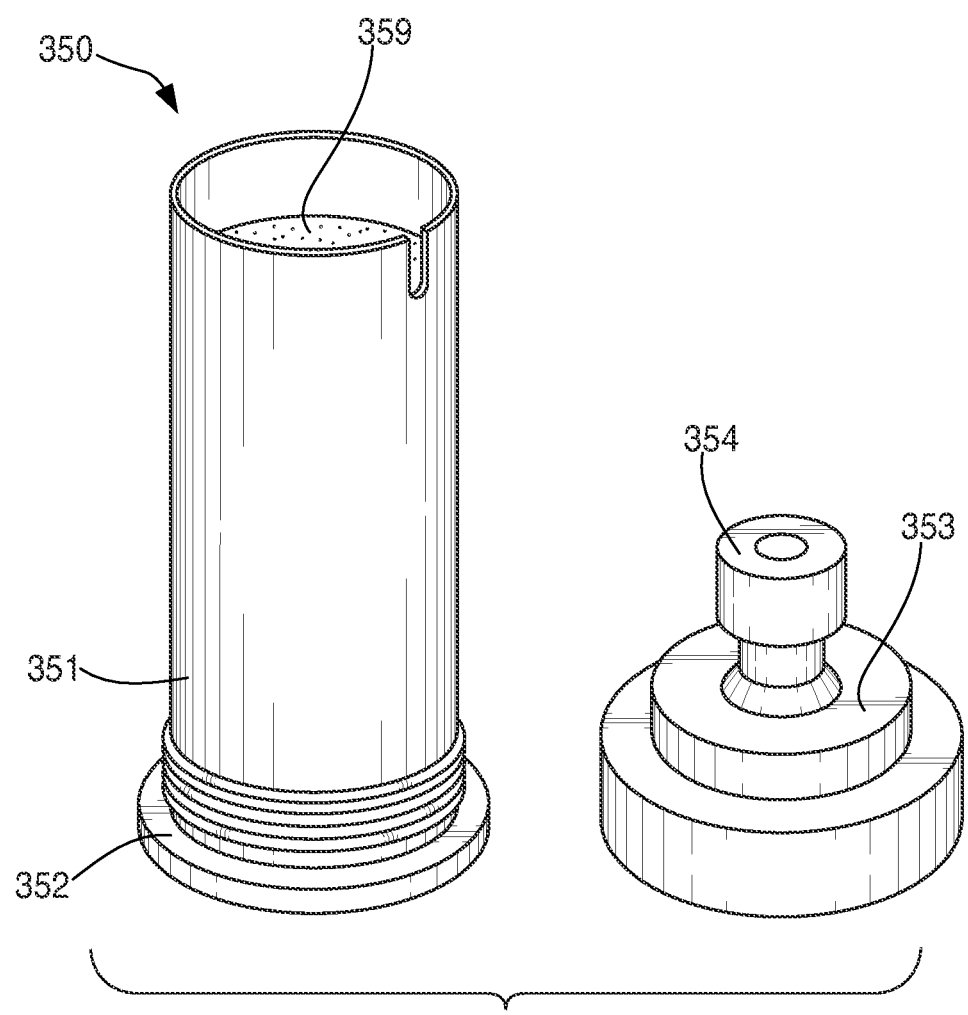
FIG. 3D shows a perspective view of various components of the base compound container of FIG. 3C, in accordance with at least one embodiment.

As shown in FIG. 3D, for example, compound container 350 can include a containing portion 351 for storing base compound 359, and one or more caps 352 for at least partially sealing containing portion 351. Compound container 350 can also include a supplying or injection cap 353 having a compound injection nozzle (or tube) 354. Caps 352 can seal lower and upper openings of compound container 350 and can be removed when base compound 359 is to be supplied or injected. For example, prior to injecting base compound 359, caps 352 can be removed, injection cap 353 can be secured (e.g., screwed) to one opening of compound container 350, and the other opening of compound container 350 can be coupled to a piston (e.g., hydraulic aggregate type piston) (not shown) of supplying device 340. Compound container 350 can be configured to store any suitable amount of base compound 359 required to produce an arch device, such as arch device 100 or 200. When compound container 350 is coupled to supplying device 340, base compound 359 can be supplied to or injected into mold device 301, as shown in FIG. 3C.

Each of lower and upper portions 310 and 320 of mold device 301 can be composed at least partially of metal (e.g., brass beryllium). Lower portion 310 can include an arch-shaped recess 312, and upper portion 320 can include a similar arch-shaped recess 322. As shown in FIGS. 3A and 3B, for example, recess 312 can be shaped and sized to receive inlay device 330.

Lower portion 310 can include one or more fastening passages 314 that can correspond to and can interact with or fit to fasteners 324 of upper portion 320. Additionally, lower and upper portions 310 and 320 can include openings 315 and 325 that can lead to supplying or injection slots 316 and 326, respectively. Injection slots 325 and 326 can form a supplying or injection hole 317, when lower and upper portions 310 and 320 are coupled to one another. Injection hole 317 can be large enough to receive at least a portion of injection nozzle or tube 354 of compound container 350. Each of lower and upper portions 310 and 320 can also include ends 319 and 329, respectively, that protrude slightly from a corresponding body of lower and upper portions 310 and 320. Ends 319 and 329 can be gripped or held onto to decouple lower and upper portions 310 and 320 from one another (described in more detail below).

In at least one embodiment, mold device 301 can be constructed by using a master arch device. For example, mold device 301 can be constructed by using one or more off-the-shelf or master dentures that have certain portions (e.g., base material or flange portion) removed to form a suitably sized and shaped master arch device (e.g., similar to arch devices 100 and 200). The master arch device can be used to create each of lower and upper portions 310 and 320 so as to form appropriately sized and shaped recesses 312 and 322. In this way, when mold device 301 is used to manufacture other arch devices, a resulting arch device can have a size, a shape, and structural features similar to that of the master arch device.

In some instances, mold 301 can also be a dedicated mold used to fabricate the teeth (e.g., teeth 120). Mold 301 can have respective receptors (not shown) in recess 312 corresponding to each tooth. Each of these receptors can be shaped and sized according to the desired anatomy of the corresponding tooth. As part of fabricating the teeth, one or more compounds can be supplied into mold 301 so as to fill each of the teeth receptors and form the respective teeth. The teeth can subsequently be removed from mold 301 by blowing air thereon. Additionally, the teeth can then be finished by polishing or other finishing processes.

The structure of mold device 301 can be rigid, and thus, can limit the variability in the dimensions or tolerance of each fabricated tooth (e.g., to about 2 micrometers). However, any polishing of the teeth can change their shape and size, and thus increase their dimensional variabilities. This can prevent the teeth from fitting snugly back into the respective teeth receptors of mold 301 during later arch device fabrication. When this increase in dimensional tolerance is not desired, the teeth may not be polished. However, when polishing is desired, inlay device 330 can be employed to provide the added tolerance needed.

Inlay device 330 can be composed of any suitable material. For example, inlay device 330 can be at least partially composed from an inlay compound (e.g., described in more detail below), such as silicone. Inlay device 330 can include an arch-shaped tray 332. Tray 332 can include an entry point 337 configured to receive base compound 359 through injection hole 317 of mold device 301. Tray 332 can also include ears 338, which can be shaped and sized to fit into corresponding ear receptors 318 of mold device 301. This can, for example, help to align inlay device 330 with recess 312, and retain inlay device 330 in position. Tray 332 can include recess 332 that extends from one end 333 to another end 335. Recess 332 can be shaped and sized to receive a portion of base compound 358, which can form a base of a resulting arch device (e.g., any one of arch devices 100 and 200). Additionally, recess 332 can include multiple teeth receptors 336 that can each be shaped and sized to receive a particular tooth of a set of teeth. Referring briefly to FIG. 4, FIG. 4 is an example of a set of teeth 420 that can be used to form an arch device. Each tooth receptor 336 can have a depth sufficient to prevent base compound 359 from flowing into that receptor when a corresponding tooth of teeth 420 is disposed therein. That is, when a corresponding tooth is disposed in a tooth receptor, and when base compound 359 flows into recess 332, base compound 359 can only flow around a portion of that tooth, but not into the tooth receptor itself.

Referring back to FIGS. 3A-3F, in at least one embodiment, inlay device 330 can also be constructed by using a master arch device, which can be similar to the master arch device used to construct mold device 301. To create inlay device 330, for example, the master arch device can be positioned in mold device 301 (e.g., in recess 322), and an inlay compound (described in more detail below) can be injected into injection hold 317 of mold device 301. Since the master arch device may not occupy the entire empty volume within mold device 301 (e.g., the master arch device may not occupy recess 312), the injected inlay compound can fill these empty areas, and can be cured therein. When mold device 301 is subsequently opened, inlay device 330, having a footprint of tooth recesses that correspond to the teeth of the master arch device, can be removed from mold device 301.

In at least one embodiment, the apparatus can also include an injection hole sealing component 360. As shown in FIG. 3A, sealing component 360 can resemble a ball, and can be composed of any suitable material. For example, sealing component can be a metal (e.g., steel) ball. During manufacture of an arch device, sealing component 360 can be inserted into injection hole 317. For example, sealing component 360 can be inserted deep enough into injection hole 317, so as to allow injection tube 354 to be insertable into injection hole 317, and to allow base compound 359 to be injectable into mold device 301 (e.g., into unoccupied areas of recesses 312 and 322). Base compound 359 can then be processed to form the base (e.g., any one of bases 110 and 210) of a resulting arch device.

In at least one embodiment, the arch fabrication apparatus can also include a polymerization press 370 for polymerizing injected base compound 359 into mold device 301. As shown in FIG. 3E, for example, polymerization press 370 can be controlled (e.g. electrically) to provide heat at a range of temperatures, and can include, among other features, a heating portion 372 that can receive and fit to mold device 301 for heating base compound 359.

Although not shown, in at least one embodiment, an arch device fabrication apparatus can also include one or more post-processing tools for post-processing an arch device formed in mold device 301. For example, these post-processing tools can include one or more polishing and trimming tools for removing excess material from, and finishing the arch device.

Figure 3F:
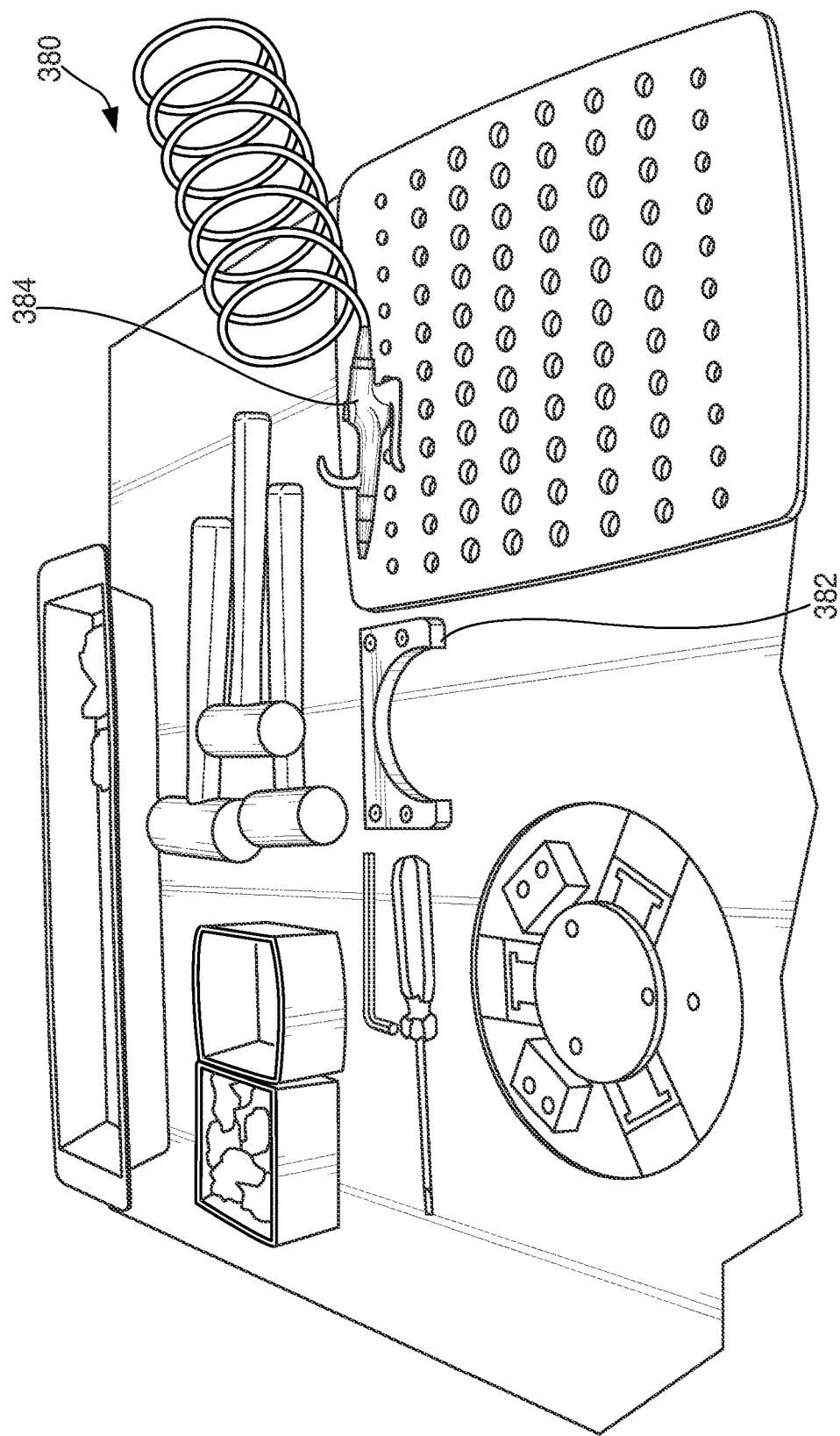
FIG. 3F is a perspective view of a demoulding kit for demoulding a mold device, in accordance with at least one embodiment.

Moreover, in at least one embodiment, the arch device fabrication apparatus can also include a demoulding kit for uncoupling lower and upper portions 310 and 320 from one another. As shown in FIG. 3F, for example, a demoulding kit 380 can include a demoulding device 382, a compressed air supply device 384, and various other tools (e.g., hammers, etc.) that can be useful in decoupling lower portion 310 from upper portion 320. In at least one embodiment, demoulding device 382 can include a slot for engaging either one of end 319 of lower portion 310 of mold 301 and end 329 of upper portion 320 of mold 301. For example, after device 382 is engaged to either end 319 or 329, pressure can be applied to separate lower and upper portions 310 and 320. In at least another embodiment, pneumatically powered pistons (not shown) can be used to push against each of ends 319 and 329 to separate lower and upper portions 310 and 320. When lower and upper portions 310 and 320 are uncoupled, a resulting arch device formed in mold device 301 can subsequently be removed from mold device 301.

It should be appreciated that not all of the components shown in FIGS. 3A-3F may be required during fabrication of an arch device. For example, in at least one embodiment, inlay device 330 may not be employed during fabrication of an arch device. In these embodiments, the teeth (e.g., teeth 120 or 420) can be disposed directly into respective receptors (not shown) of recess 312 of lower portion 310 that are shaped with minimal tooth anatomy (e.g., a slightly larger receptor for each tooth). This can avoid some of the above-described tolerance issues with processed teeth and can allow mold 301 to be used for general tooth production.

It should also be appreciated that other components or devices can be employed in each step of the fabrication of an arch device. Additionally, although FIG. 3A only shows lower and upper portions 310 and 320 each having a single recess, respectively, it should be appreciated that each of lower and upper portions 310 and 320 can include more than one recess. For example, lower portion 310 can include two or more recesses similar to recess 312, and upper portion 320 can include two or more recesses similar to recess 320. In this manner, mold device 301 can be employed to simultaneously fabricate multiple arch devices.

It should be appreciated that different molds (e.g. similar to mold device 301) can be provided. For example, different teeth laboratories can fabricate teeth of different shapes and sizes. Different molds can thus be constructed to accommodate these teeth.

Additionally, although an apparatus for fabricating an arch device has been described above with respect to FIGS. 3A-3F, it should be appreciated that a similar apparatus can be provided to fabricate a partial arch device (e.g., such as the partial arch device described above).

Moreover, a similar apparatus can be provided to fabricate other dental devices, such as a denture, a denture form device, and the like.

Figure 5:
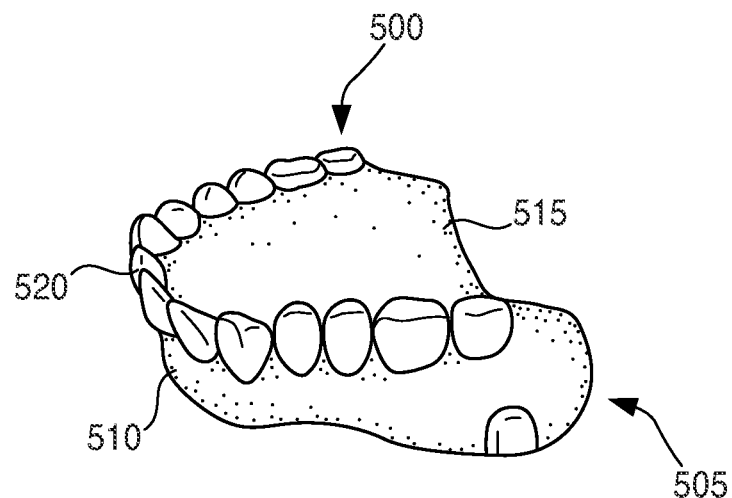
FIG. 5 shows a front perspective view of a denture form device, in accordance with at least one embodiment.

FIG. 5 shows a perspective view of a denture 500 (e.g., a mandibular denture). As shown in FIG. 5, denture 500 can be larger than any one of arch devices 100 and 200, and can include a unitary structure 505 having a base or lingual portion 510 and a flange portion 515, and a set of teeth 520 integrated to one side of base portion 510. Flange portion 515 can provide a framework for maintaining the structural integrity of denture 500.

Figure 6:
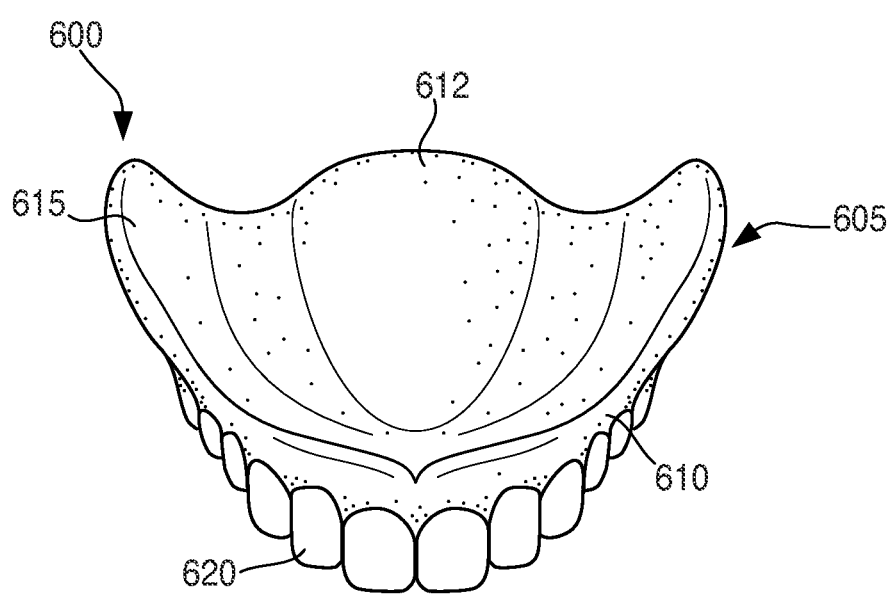
FIG. 6 shows a perspective view of a denture, in accordance with at least one embodiment.

FIG. 6 shows a perspective view of a denture form device 600 that can be adjustable, similar to an arch device (e.g., arch devices 100 and 200). However, whereas an arch device may not include a flange portion (e.g., base material of a denture, such as flange portion 515 of denture 500), denture form device 600 can include such a portion. Thus, denture form device 600 can resemble an actual denture in shape and size. As shown in FIG. 6, for example, denture form device 600 can include a unitary structure 605 having a base or lingual portion 610 and flange portion 615, and a set of teeth 620 disposed on base or lingual portion 610, similar to an actual denture (e.g., denture 500).

Rather than being substantially rigid and inflexible as actual dentures tend to be, denture form device 600 can be composed of one or more materials that can become flexible or adjustable when subjected to heat. For example, denture form device 600 can be at least partially composed of thermoplastic, and can become at least partially adjustable when heated in warm or hot water (e.g., at about 175° F.), similar to arch devices 100 and 200. Moreover, as shown in FIG. 6, denture form device 600 can include a bump or fold 612 that can further allow denture form device 600 to adjust when heated. For example, bump 612 can allow adjustment of a width of the arch shape of base portion 610.

Denture form device 600 can be used as a temporary or permanent denture. In at least one embodiment, denture form device 600 can be selected, processed (e.g., trimmed), and subjected to heat for a predefined time (e.g., immersed in hot water at about 175° F. for about three minutes). When heated, denture form device 600 can be adjustable in shape (e.g., the width of the arched base portion can be adjusted). In this adjustable state, denture form device 600 can be inserted into a patient's mouth, coupled to a corresponding portion of the mouth, and adjusted as needed. After denture form device 600 is adjusted, it can be processed and used as a model to form a wax try-in or finished denture. As some examples, the borders of adjusted device 600 can be trimmed, final impressions can be made (e.g., using alginate), teeth mold, shade, and position can be selected, vertical dimensions can be established, and bite can be registered.

Because of its adjustability, denture form device 600 can also be used to obtain a physical model of a patient's maxillary jaw. For example, denture form device 600 can be used as a denture data point acquisition device, which can acquire information needed to fabricate an actual denture.

Although FIG. 6 only shows a maxillary denture form device, it should be appreciated that a similar mandibular denture form device (not shown) can also be provided, and can also be used to obtain a physical model of a patient's mandibular jaw.

Figure 7:
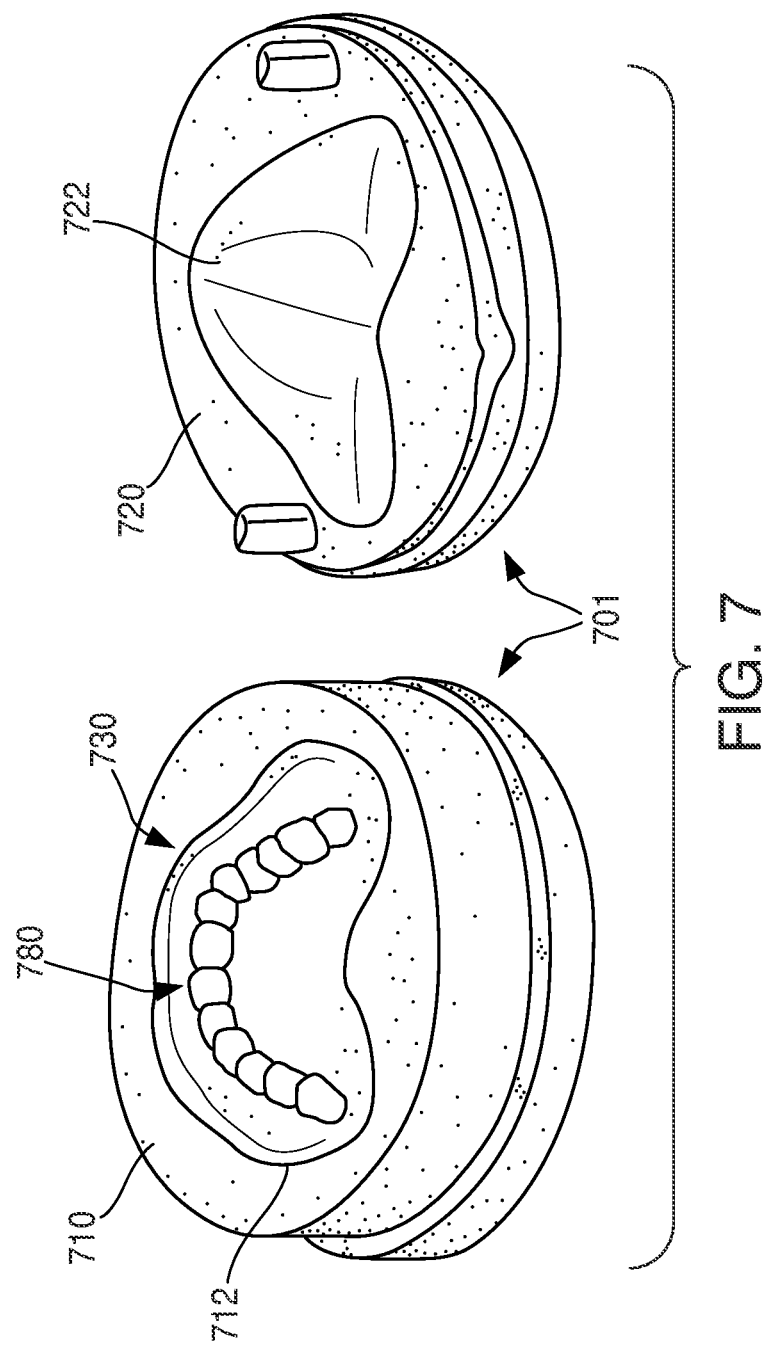
FIG. 7 is a perspective view of lower and upper portions of another mold device, including another inlay device and another set of teeth, in accordance with at least one embodiment.

As shown in FIGS. 5 and 6, a denture and a denture form device can be larger than an arch device, since they can each include base material or a flange portion not included in an arch device. Thus, a mold having larger recesses (e.g., larger than recesses 312 and 322) can be employed to fabricate these devices. FIG. 7 is a perspective view of lower and upper portions 710 and 720, respectively, of a mold device 701, including an inlay device 730 and teeth 780. Mold device 701 can be similar to mold device 301, inlay device 730 can be similar to inlay device 330, and teeth 780 can be similar to teeth 420. As shown in FIG. 7, however, lower and upper portions 710 and 720 can include larger recesses 712 and 722, respectively, than recesses 312 and 322, which can accommodate more of a base compound (e.g., base compound 359) to form a larger dental device.

Figure 8:
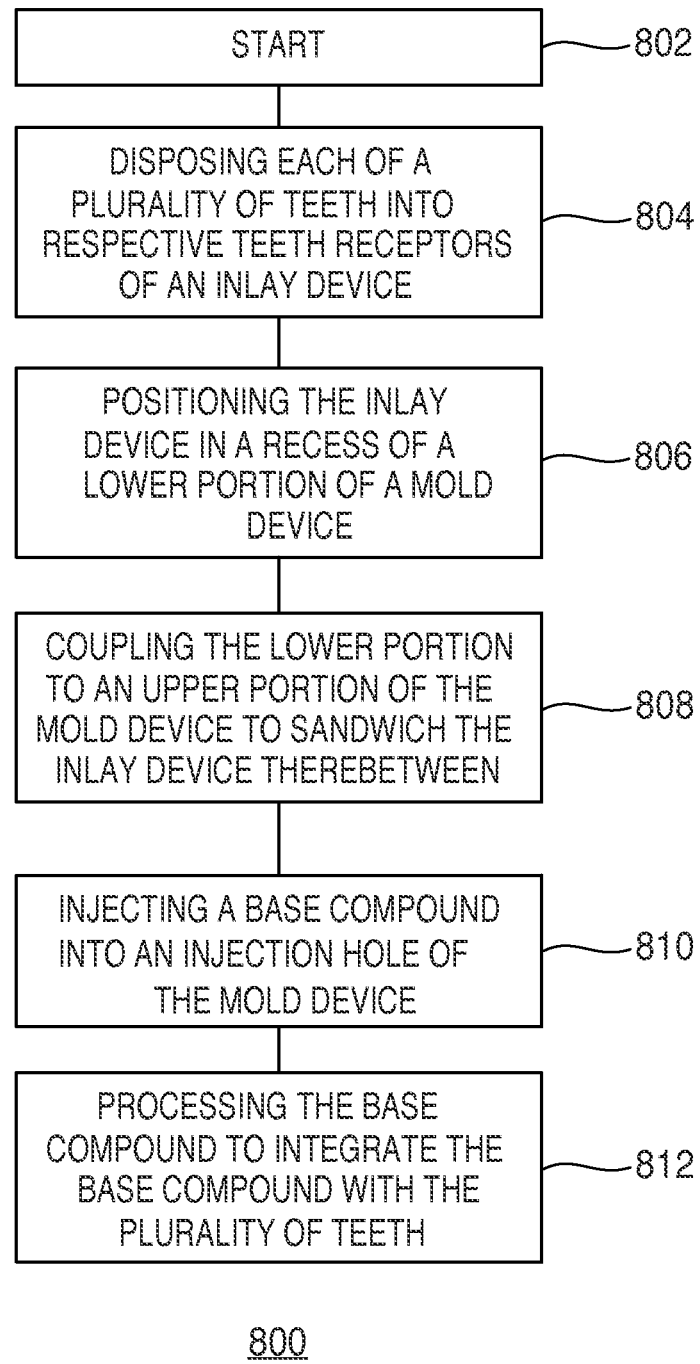
FIG. 8 is an illustrative process for constructing an arch device, in accordance with at least one embodiment.

FIG. 8 is an illustrative process 800 for constructing an arch device (e.g., any one of arch devices 100 and 200). Process 800 can begin at step 802. At step 804, the process can include disposing each of a plurality of teeth into respective teeth receptors of an inlay device. For example, the process can include disposing each of a plurality of teeth 420 into respective teeth receptors 336 of inlay device 330. In at least one embodiment, the teeth can be pre-arranged in a predefined order in various containers of a teeth tray (e.g., as shown in FIG. 4) such that they can be easily accessible during the fabrication of the arch device.

In at least one embodiment, the process can also include, prior to or after disposing the teeth on the inlay device, applying bonding material to at least one tooth of the plurality of teeth. For example, the process can include, prior to or after disposing teeth 420 on inlay 330, applying bonding material (e.g., a monomer, etc.) to at least one tooth of teeth 420. This can assist the teeth in bonding to a later injected base compound (e.g., base compound 359).

In at least one embodiment, the process can also include, after disposing the plurality of teeth on the inlay device, adjusting a position of at least one tooth of the plurality of teeth. For example, the process can also include, after disposing teeth 420 on inlay 330, adjusting a position of at least one tooth of teeth 420 (e.g., using a tool, such as a screwdriver and the like). This can ensure that each tooth is positioned properly in the inlay, and later in a mold device.

At step 806, the process can include positioning the inlay device in a recess of a lower portion of a mold device. For example, the process can include positioning inlay device 330 in recess 312 of lower portion 310 of mold device 301.

At step 808, the process can include coupling the lower portion to an upper portion of the mold device to sandwich the inlay device therebetween. For example, the process can include coupling lower portion 310 to upper portion 320 of mold device 301 to sandwich inlay device 330 therebetween.

In at least one embodiment, the process can also include, prior to coupling the lower and upper portions together, applying a layer of mold release agent to a recess of the upper portion. For example, the process can include, prior to coupling lower and upper portions 310 and 320 together, applying a layer of mold release agent to recess 322. The mold release agent can include silicone and/or Teflon, which can assist in separating a base (e.g., such as base 110 or 210, formed from base compound 359) from the upper portion of the mold device at a later stage of the process. In at least one embodiment, the process can also include applying a layer of mold release agent to the recess of the lower portion of the mold device as well.

In at least one embodiment, the process can also include, prior to coupling the lower and upper portions together, positioning a sealing component in any one of an injection slot of the lower portion and an injection slot of the upper portion of the mold device. For example, the process can include, prior to coupling lower and upper portions 310 and 320 together, positioning sealing component 360 in any one of injection slots 325 and 326.

At step 810, the process can include injecting a base compound into an injection hole of the mold. For example, the process can include injecting base compound 359 into injection hole 317 of mold device 301. As described above with respect to FIGS. 3A-3F, compound container 350 can be coupled to base compound supplying device 340 to supply or inject base compound 359 into mold device 301. This can be accomplished by coupling a piston (not shown) of supplying device 340 to one end of compound container 350 (e.g., that is opposite the end of container 350 to which injection cap 353 is coupled), and controlling the piston to force base compound 359 out of injection nozzle 354. This step can continue until some of the injected base compound begins to overflow out of injection hole 317 (e.g., around openings 315 and 325).

In at least one embodiment, prior to injecting the base compound, the process can also include increasing a temperature of the base compound. For example, prior to injecting base compound 359 (which may have been subjected to lower temperatures, at or near freezing), the process can include increasing the temperature of base compound 359. More particularly, the process can include increasing the temperature of compound container 350.

In at least one embodiment, prior to injecting the base compound, the process can also include releasing any air that may exist in an injection nozzle of a base compound supplying device to prevent the air from being injected into the mold device. For example, prior to injecting base compound 359, the process can also include releasing any air that may exist in injection nozzle 354 of compound container 350 when coupled to base compound supplying device 340 to prevent the air from being injected into mold device 301.

At step 812, the process can include processing the base compound to integrate the base compound with the plurality of teeth. For example, the process can include processing injected base compound 359 to integrate base compound 359 with teeth 420. More particularly, the process can include polymerizing base compound 359 using polymerization press 370. For example, mold device 301 can be coupled to heating portion 372 of polymerization press 370, and can be subjected to one or more heat cycles at a predefined temperature. For example, mold device 301 can be heated by polymerization press 370 for approximately six minutes at approximately 125° C. After polymerization, the process can also include cooling the mold. For example, the process can include cooling mold device 301 by submersing mold device 301 in cold tap water for about four minutes.

In at least one embodiment, the process can also include demoulding the mold device. For example, the process can include demoulding mold device 301 (e.g., by separating lower portion 310 from upper portion 320). particularly, the process can include removing one or more fasteners between the lower and upper portions of the mold. For example, the process can include removing fasteners 324 from fastening passages 314. When mold device 301 is demoulded, an arch device (e.g., similar to arch devices 100 and 200), that is formed by the processed base compound 359 and teeth 420, can be accessed.

In at least one embodiment, a demoulding device (e.g., demoulding device 382) can be employed to separate the lower and upper portions of the mold device. In these embodiments, the process can include engaging the demoulding device to predefined portions of the mold. For example, the process can include engaging demoulding device 382 (e.g., via a slot of device 382) to any one of ends 319 and 329. The process can also include applying force to the demoulding device to separate the lower and upper portions. For example, the process can also include applying force to demoulding device 392 to separate lower and upper portions 310 and 320. In at least another embodiment, the process can additionally, or alternatively, include engaging one or more pneumatically powered pistons to ends 319 and 329 to apply opposite forces thereon to separate lower and upper portions 310 and 320.

In some instances, the resulting arch device, formed from the integrated base compound and teeth, can be adhered or stuck to the upper portion after demoulding. To remove the arch device from the upper portion, the process can include applying a force onto the arch device to separate the arch device from the upper portion. For example, the process can include applying a force (e.g., via compressed air, via one or more of a soft metal screw driver and a hammer, etc.) to the arch device to separate the arch device from upper portion 320.

In at least one embodiment, after demoulding, the process can include processing the arch device. For example, after demoulding mold device 301, the process can include processing one or more of arch devices formed from integrated base compound 359 and teeth 420. Processing can include inspecting, trimming, cleaning, and polishing the arch device. For example, the process can include inspecting the arch for damage or distortions in shape. As another example, the process can include removing any excess material from the arch device. This can involve using one or more of a high-speed grinder, an acrylic bur, a blowing tool, and an arbor band on a Baldor Lathe to flash, blow, or trim off the excess material. As yet another example, the process can include adding one or more base materials to the base of the arch to form a denture, and then polishing the resulting denture. The polishing can involve applying a medium and fine grit flours of pumice to select portions of the arch device via a rag wheel (not shown). Additionally, or alternatively, this can also involve applying a final luster acrylic polish to select portions of the arch device via a rag wheel (also not shown). It should be appreciated that any suitable portion of the resulting denture can be polished.

In at least one embodiment, the process can also include cleaning the mold and inlay devices. For example, the process can include cleaning mold device 301 (e.g., recesses 312 and 322 of lower and upper portions 310 and 320, respectively) and inlay device 330. This can ensure that the mold and inlay devices are still structurally suitable for use in fabricating further arch devices.

Although process 800 has been described above for making an arch device, it should be appreciated that a similar process can be employed to make other dental devices, such as a denture or a denture form device. For example, mold 501 and inlay 530 can be employed to fabricate one or more of these dental devices. Because various steps to fabricate these dental devices can be similar to those for an arch device, their description is not repeated.

Figure 9:
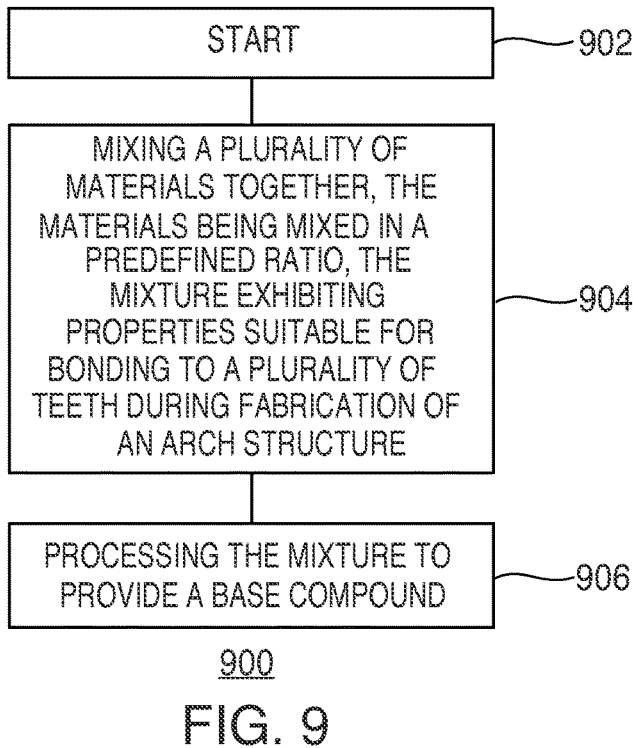
FIG. 9 is an illustrative process for fabricating a base compound, in accordance with at least one embodiment.

FIG. 9 is an illustrative process 900 for fabrication a base compound (e.g., base compound 359 suitable for use in fabricating an arch device). Process 900 can begin at step 902. At step 904, the process can include mixing a plurality of materials together, the materials being mixed in a predefined ratio, and the mixture exhibiting properties suitable for bonding to a plurality of teeth during fabrication of the arch device. For example, the process can include mixing a plurality of materials together that have properties suitable for forming at least a base portion of an arch (e.g., base 110 of arch 100) and suitable for bonding to a plurality of teeth (e.g., teeth 120) during the fabrication of the arch device. Because the resulting base compound can form a base of an adjustable arch device, it can be preferable to select materials or compounds that allow a resulting base to behave in certain ways when manipulated (e.g., when subjected to different temperatures.

In at least one embodiment, the materials can include a polymer and a monomer (e.g., a pre-mixed monomer-plasticizer in the form of a clear liquid), which can be processed to form acrylic thermoplastic. These materials or compounds can be mixed in a predefined ratio, such as, for example, 63.5% polymer and 36.5% monomer, by weight. For example, the process can include weighing and mixing predefined amounts of the polymer (e.g., 381 grams) and monomer (e.g., 219 grams) in a mixing apparatus for a predetermined time (e.g., for a time sufficient to ensure that no dry polymer remains at the lower end of the mixing apparatus). The mixture can be prepared in any amount suitable to fill one or more compound containers (e.g., compound container 350).

At step 906, the process can include processing the mixture to provide the base compound. For example, the process can include processing the mixture of polymer and monomer to provide the base compound. In the embodiments described above, where polymer and monomer are used in the mixture of materials or compounds, the process can include sealing the mixing apparatus to allow the mixture to change from a relatively thick dispersion to a homogenous dough-like mixture, which can be suitable for forming a base of an arch device (e.g., base 110 of arch device 100).

When polymer and monomer are selected as the materials or compounds of the mixture, the process can also include maintaining the sealed mixing apparatus at a relatively constant temperature (e.g., in a freezer or a temperature-controlled room). When the sealed mixing apparatus is maintained at a lower temperature (e.g., below 25° C.) for a prolonged period of time, the monomer can at least partially separate from the plasticizer, can be absorbed by the polymer, and some of the plasticizer can rise relative to the rest of the mixture. To prevent this from occurring, the process can also include occasionally stirring the mixture until the mixture becomes a dough-like base compound (e.g., base compound 359). The base compound can be transferred from the mixing apparatus to one or more compound containers (e.g., compound containers 350), which can then be sealed (e.g., with respective caps 352). Where the need arises, the process can also include lowering the temperature (e.g., by freezing) of the compound containers to prevent the base compound from thickening or undergoing polymerization. In some instances, it can be preferable to use the base compound within about twenty minutes after it is removed from a freezer to prevent the base compound from transforming into a liquid.

As described above, an inlay device (e.g., inlay devices 330 and 530) can be produced from an inlay compound. The inlay compound can be formed using any suitable process, and can be composed of any suitable type of material. In at least one embodiment, it can be desirable for the inlay compound to behave in certain ways under different conditions when used during the fabrication of an arch device. For example, it can be desirable for the inlay compound to be capable of providing sufficient retaining force to teeth (e.g., teeth 420) during an arch device fabrication process, such that the teeth do not shift in position. To provide this, the inlay compound should exhibit at least a predefined hardness.

As another example, it can be desirable that the inlay compound withstand sufficient wear and tear during a demoulding step in an arch fabrication process (e.g., the demoulding step of process 800). To provide this, the inlay compound should exhibit at least a predefined resistance to various forces when hardened. As yet another example, it can be desirable that the inlay compound be curable in a short amount of time.

In at least one embodiment, the inlay compound can include silicone. In addition to silicone, the inlay compound can also include an activator that functions as a catalyst. The silicone can include one or more types of silicone. For example, the silicone can include one or more of P-60 and P-70 from Silicones, Inc. P-60 and P-70 can have a hardness of at least 65, which can provide sufficient retaining force to teeth in a mold, and can withstand certain wear and tear during demoulding of the mold. Moreover, P-60 and P-70 can also cure relatively quickly (e.g., in about twenty minutes at 120° C.), can withstand heat during the fabrication of an arch device, and can resist from chemically interacting with a base compound (e.g., base compound 359).

Figure 10:
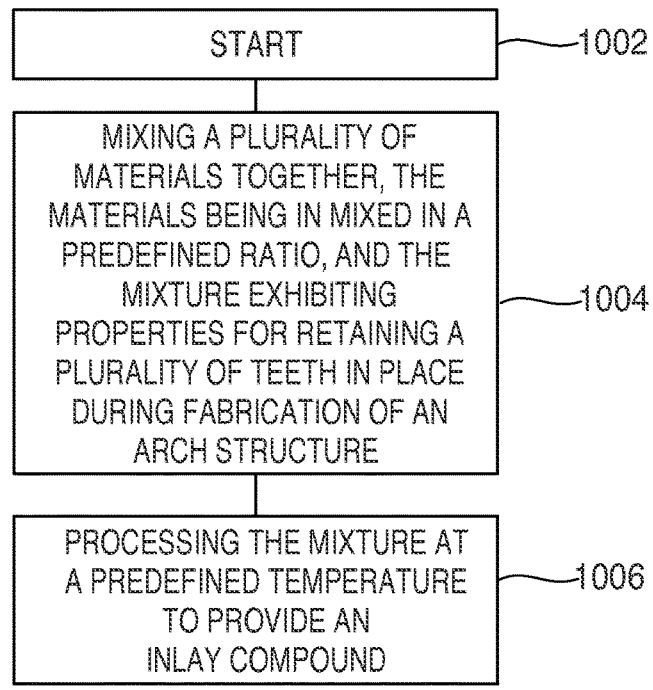
FIG. 10 is an illustrative process for fabricating an inlay compound, in accordance with at least one embodiment.

FIG. 10 is an illustrative process 1000 for fabricating an inlay compound. Process 1000 can begin at step 1002. At step 1004, the process can include mixing a plurality of materials together, the materials being mixed in a predefined ratio, and the mixture exhibiting properties for retaining a plurality of teeth in place during fabrication of an arch device. For example, the process can include mixing P-60 (or P-70) and an activator together in a predefined ratio (e.g., ten parts P-60 (or P-70) to one part activator). The mixture can exhibit properties for retaining teeth (e.g., teeth 420) during the fabrication of an arch device (e.g., arch device 100 or 200).

At step 1006, the process can include processing the mixture at a predefined temperature to provide the inlay compound. For example, the process can include subjecting the mixture under a vacuum (e.g., by degassing under a vacuum of at least 29 inches of mercury for a few minutes).

Figure 11:
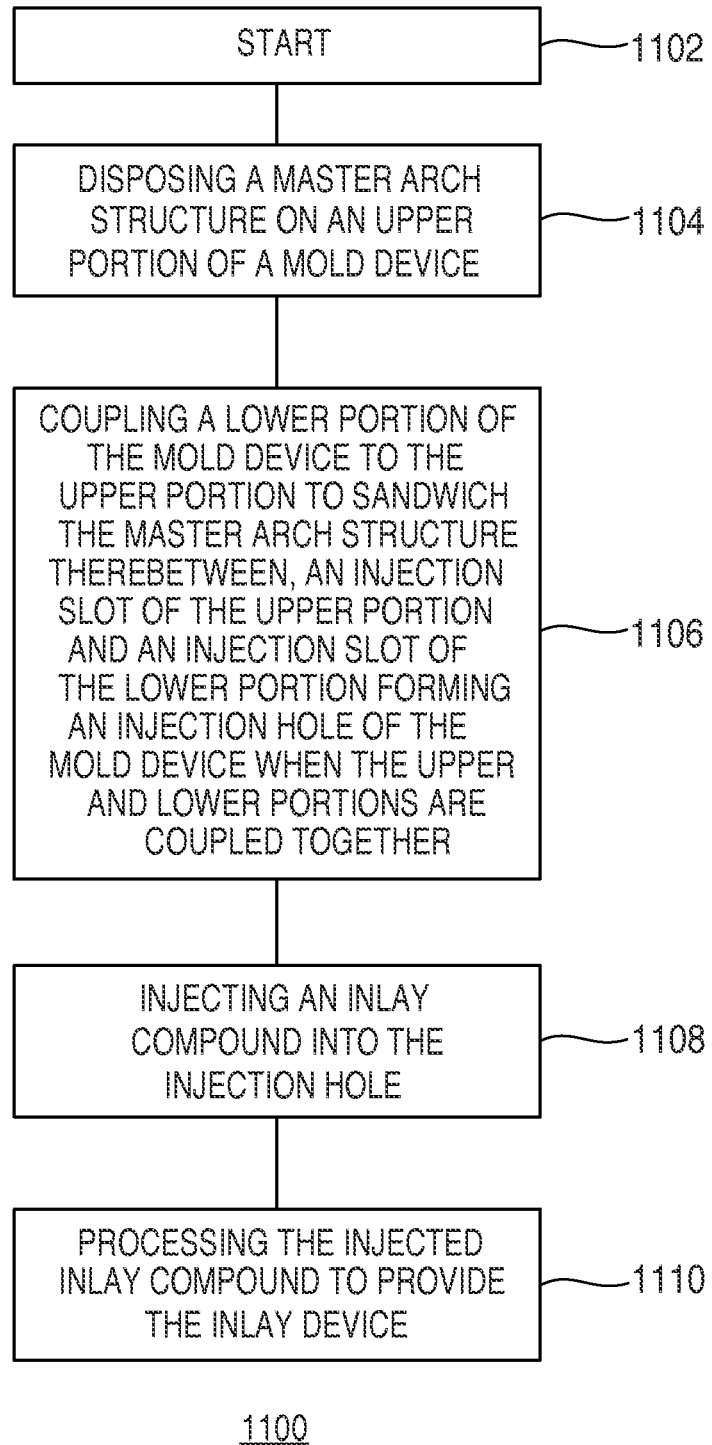
FIG. 11 is an illustrative process for constructing an inlay device, in accordance with at least one embodiment.

FIG. 11 is an illustrative process 1100 for constructing an inlay device (e.g., similar to inlay device 330). Process 1100 can be similar to process 800 and can employ an inlay device fabrication apparatus similar to arch device fabrication apparatus described above with respect to FIGS. 3A and 3B. The inlay device fabrication apparatus can include one or more components that can be the same as or similar to those of the arch device fabrication apparatus. For example, the inlay device fabrication apparatus can include mold device 301 and compound container 350, or a similar mold device and a similar compound container.

Process 1100 can begin at step 1102. At step 1104, the process can include disposing a master arch device on an upper portion of a mold device. For example, the process can include disposing a master arch device, which can be similar to arch device 100 or 200, on upper portion 320 of mold device 301. More particularly, the process can include disposing the master arch device on recess 322 of upper portion 320.

At step 1106, the process can include coupling a lower portion of the mold to the upper portion to sandwich the master arch device, where an injection slot of the lower portion and an injection slot of the upper portion forms an injection hole of the mold device when the lower and upper portions are coupled together. For example, the process can include coupling lower portion 310 of mold device 301 to upper portion 320 to sandwich the master arch device, where injection slot 316 of lower portion 310 and injection slot 326 of upper portion 320 form injection hole 317 when lower and upper portions 310 and 320 are coupled together. This coupling step can be similar to the coupling of lower and upper portions of a mold device described above with respect to FIG. 8.

In at least one embodiment, the process can include, prior to coupling the lower and upper portions of the mold device together, applying a mold release agent to select areas of the lower and upper portions. For example, the process can include applying a mold release agent (e.g., Teflon) to select portions of lower and upper portions 310 and 320 of mold device 301. Additionally, prior to the coupling in step 1106, the process can also include positioning a sealing component in any one of an injection slot of the lower portion and an injection slot of the upper portion of the mold. For example, this positioning step can be similar to the positioning step described above with respect to FIG. 8.

At step 1108, the process can include injecting an inlay compound into the injection hole. For example, the process can include injecting an inlay compound (described in more detail below) into injection hole 317. This injection step can be similar to the injection of a base compound into a mold device described above with respect to FIG. 8. In at least one embodiment, the inlay compound can be injected until the inlay compound fills empty areas within the mold device, and reaches injection slots of the lower and upper portions of the mold device. More particularly, the inlay compound can be injected until it fills recess 312 and reaches injection slots 316 and 326 (e.g., an inner opening end of injection hole 317). A different material can subsequently be injected to fill the entirety of injection slots 316 and 326 (and thus, injection hole 317). For example, acrylic or a compound similar to base compound 359 can be used to fill the injection slots. In this manner, the material (e.g., acrylic) can prevent the inlay device from potential tearing during a demoulding step at a later stage in the process.

Figure 12:
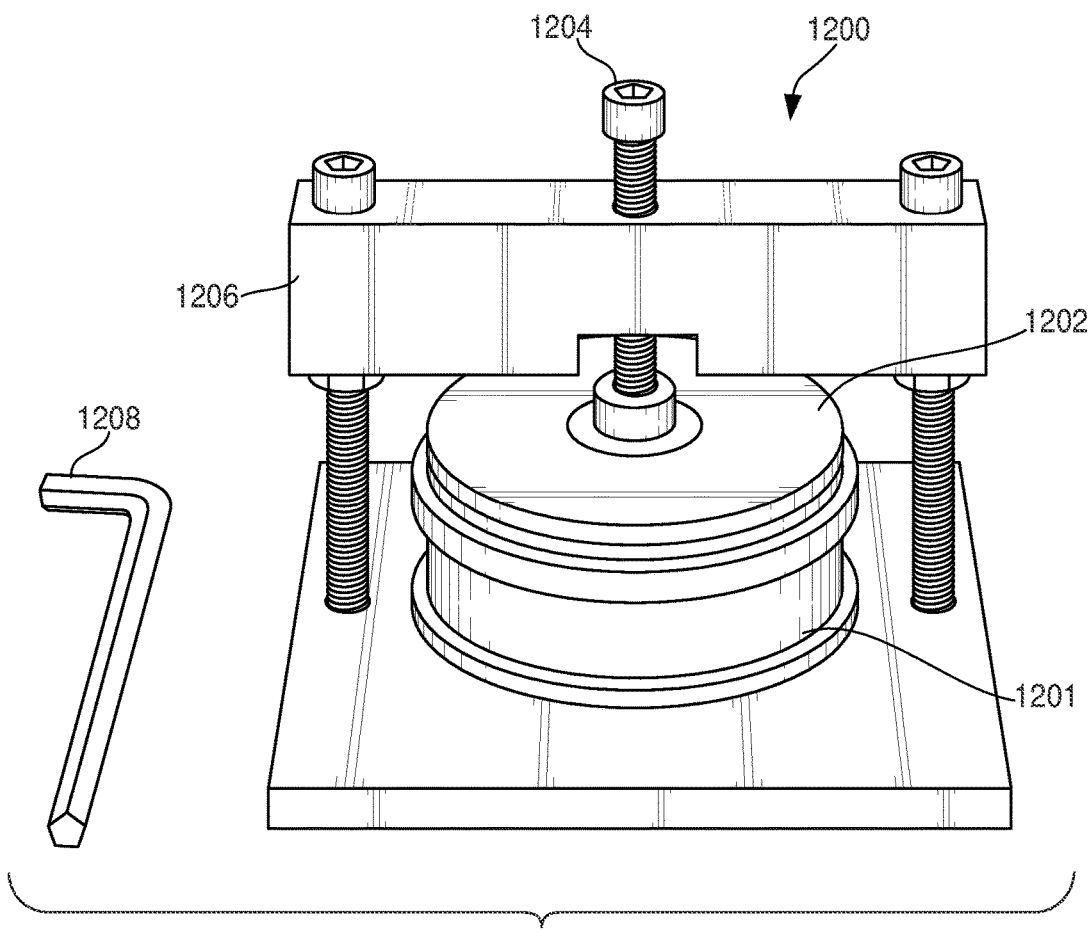
FIG. 12 shows a front perspective view of a clamping device coupled to a mold device, in accordance with at least one embodiment.

At step 1110, the process can include processing the injected inlay compound to provide the inlay device. For example, the process can include processing the injected inlay compound to provide inlay device 330. This can involve clamping the mold to keep the mold under pressure, and subjecting the mold (and thus the injected inlay compound) to heat for a predefined time (e.g., approximately 30 minutes). FIG. 12 shows a front perspective view of a clamping device 1200 coupled to a mold 1201 (which can be similar to mold device 301). Clamping device 1200 can be used to keep the mold under pressuring during heating. As shown in FIG. 12, clamping device 1200 can include a plate 1202 and a bolt 1204 secured to a base 1206. Bolt 1204 can be screwed through a portion of base 1206. With a key 1208, bolt 1204 can be released upward or screwed downward to push plate 1202 toward mold 1201.

Figure 13:
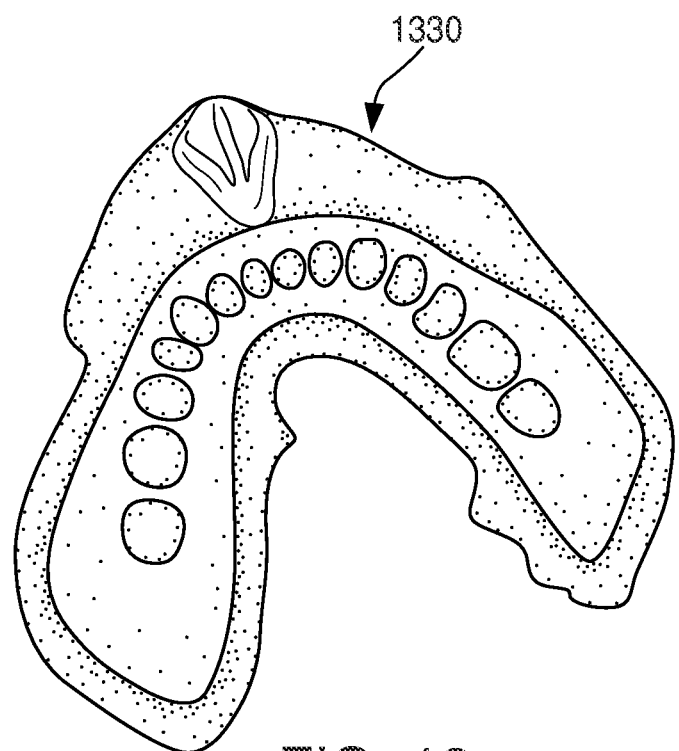
FIG. 13 is a perspective view of an inlay device that is accessible in a mold device after demoulding the mold device, in accordance with at least one embodiment.

Referring back to FIG. 11, in at least one embodiment, the process can include, after processing the inlay compound, demoulding the mold device to access an inlay device. For example, the process can include, after processing the inlay compound, demoulding mold device 301 to access an inlay device that can be similar to inlay device 330. This demoulding step can be similar to the demoulding of mold device 301 described above with respect to FIG. 8. FIG. 13 is a perspective view of an inlay device 1330 that can be accessible after demoulding a mold device. For example, inlay device 1330 can be formed from an inlay compound injected into a mold device, and can be accessible after demoulding the mold device. Inlay device 1330 can be similar to inlay device 330, but does not include an entry point (e.g., similar to entry point 337) and that does not include ears (e.g., similar to ears 338).

Referring back to FIG. 11, in at least one embodiment, after demoulding, the process can include processing the inlay device. For example, after demoulding mold device 301, the process can include processing inlay device 1330. Processing can include one or more of inspecting, trimming, and cleaning the inlay device. For example, the process can include inspecting the inlay for damage, air bubbles, or distortions in shape. As another example, the process can include trimming any flash from the inlay device. As yet another example, the process can include trimming off portions of the inlay device to form an entry point and at least one ear. Continuing with the example, the process can include trimming of portions of inlay device 1330 to form an entry point (e.g., similar to entry point 337 of inlay device 330) and ears (e.g., similar to ears 338 of inlay device 330). More particularly, the process can include trimming portions of inlay device 1330 such that the entry point aligns with an injection slot of the lower portion of the mold (e.g., injection slot 316 of lower portion 310 of mold device 301). The entry point can align with the injection slot such that a base compound (e.g., base compound 359) injected during fabrication of an arch device does not obstruct and displace with inlay device 1330 during injection. Referring briefly to FIG. 3B, for example, entry point 337 can expand towards an inside of inlay device 330, such that any injected base compound can flow smoothly into inlay device 330. Returning to FIG. 11, the process can also include trimming portions of inlay device 1330 such that the ears can fit in corresponding ear receptors of the mold device (e.g., similar to ear receptors 318 of mold device 301).

In at least one embodiment, the process can also include cleaning the mold and inlay devices. For example, the process can include cleaning mold device 301 (e.g., recesses 312 and 322 of lower and upper portions 310 and 320, respectively) and the inlay device.

Although process 1100 has been described above for making an inlay device suitable for use in fabricating an arch device, it should be appreciated that a similar process can be employed to make an inlay device suitable for use in fabricating a denture or any device shaped like a denture. For example, denture 500 or denture form device 600 can be used as a master cast or device for fabricating an inlay device suitable for use in fabricating similar dental devices. More particularly, a mold device, such as mold device 701 of FIG. 7, can be employed along with denture 500 or denture form device 600 to fabricate an inlay device similar to inlay device 730 of FIG. 7. The fabrication of an inlay device, such as inlay device 730, can be similar to the process for fabricating in inlay device, such as inlay device 330, and thus, its description is not repeated.

As described above, it may be difficult to use a rigid mold device (such as a metal mold device) to fabricate a dental device, since the teeth receptors of a rigid mold device may not tolerate large variabilities in teeth dimensions. Although an inlay device (e.g., inlay device 330 or 730) can be used to absorb some of this variability, an epoxy mold device substantially similar to the original mold device can be made and employed to fabricate dental devices. In this way, an inherent inlay area can be provided in the resulting epoxy mold device for accommodating variabilities in the dimensions of teeth.

Figure 14A:
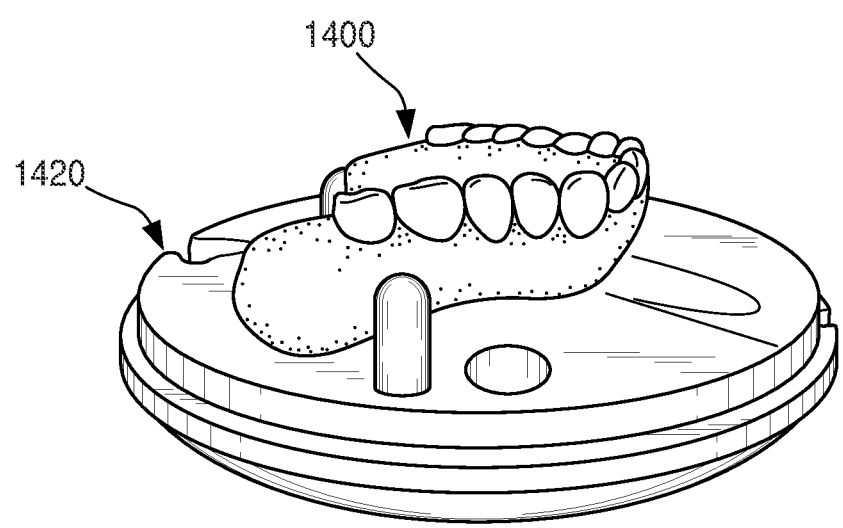
FIG. 14A shows perspective views of a master denture coupled to an upper portion of a mold device, in accordance with at least one embodiment.
Figure 14B:
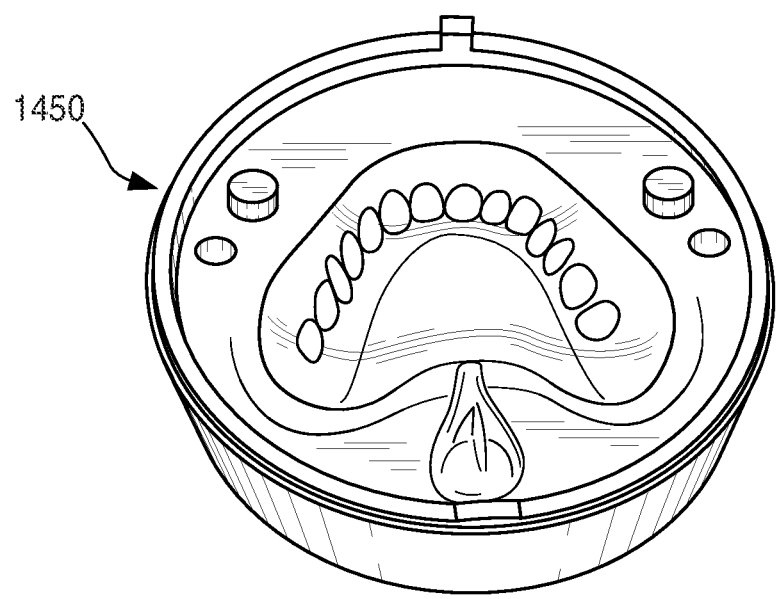
FIG. 14B shows a top perspective view of a silicone lower portion of a mold device that can be formed from silicone poured over the master denture and the upper portion of the mold device of FIG. 14A, in accordance with at least one embodiment.

FIG. 14A shows perspective views of a master denture 1400 coupled to an upper portion 1420 of a mold device. Denture 1400 can be similar to denture 500, and the mold device can be similar to mold device 701. In at least one embodiment, an epoxy mold device fabrication process can include using master denture 1400 and upper portion 1420 to form a complementary lower portion of an epoxy mold device. More particularly, the process can include aligning and at least partially surrounding upper portion 1420 with a tube or pipe (e.g., PVC) (not shown). The process can then include pouring silicone to fill the empty areas within the tube and around master denture 1400 and upper portion 1420. FIG. 14B shows a top perspective view of a silicone lower portion 1450 of a mold device that can be formed from the poured silicone. The silicone lower portion can then be used to form a final epoxy casting. For example, the process can include pouring epoxy onto silicone lower portion 1450 and curing the epoxy to form an epoxy upper portion of a mold device.

Figure 14C:
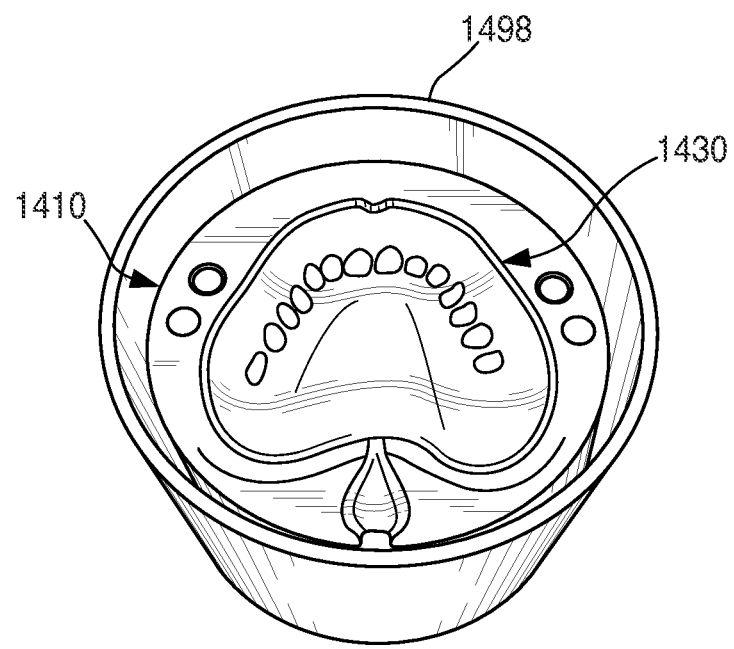
FIG. 14C shows a top perspective view of a tube at least partially surrounding a lower portion of the mold device of FIG. 14A, the lower portion having an inlay device formed and disposed therein, in accordance with at least one embodiment.

In at least another embodiment, rather than first fabricating a silicone lower portion of a mold device, and then pouring epoxy onto the silicone lower portion to form an epoxy upper portion of a mold device, the process can include sandwiching a master denture between upper and lower portions of a mold device to form an inlay device (e.g., similar to the process for forming inlay device 330), and then pouring the epoxy onto the inlay device and the lower portion of the mold device. For example, FIG. 14C shows a top perspective view of a tube 1498 at least partially surrounding a lower portion 1410 of the mold device having an inlay device 1430 formed and disposed therein. The process can include pouring the epoxy onto the surrounded lower portion 1410 and inlay device 1430, and curing the epoxy to form an epoxy upper portion of a mold device. In at least one embodiment, the process can also include, prior to the pouring, applying a coating of mold release agent to tube 1498, lower portion 1410, and inlay device 1430, and applying degassed epoxy material into or onto lower portion 1410 and inlay device 1430. The process can also include using a vibrating device to vibrate lower portion 1410, inlay device 1430, and tube 1498 to prevent air from being trapped in the poured epoxy.

It should be appreciated that, any suitable materials or compounds (e.g., other than epoxy) can also be used to fabricate a mold device. Additionally, although an epoxy mold device has been described above as being fabricated using a master denture and an upper portion of a master mold device, it should also be appreciated that similar epoxy mold devices can be fabricated using a master arch device (e.g., arch device 100 or 200) and a corresponding upper portion of a master mold device (e.g., upper portion 320 of mold device 301), a master denture form device (e.g., denture form device 600) and a corresponding upper portion of a master mold device (e.g., upper portion 720 of mold device 301), and the like.

Although the fabrication of an arch device has been described above with respect to FIG. 8, it should be appreciated that an arch device (partial or full) can also be fabricated using any other methods. These methods can include, for example, computer-aided design ("CAD"), computer-aided manufacturing ("CAM"), three-dimensional (3D) printing, and the like. Moreover, one or more of these methods can also leveraged to fabricate other dental devices (e.g., denture form device 600), as well as partial and full dentures (e.g., dentures 500 and 1400).

Computer-aided design ("CAD") and computer-aided manufacturing ("CAM") systems can deliver products rapidly and with unprecedented accuracy of fit. These systems have been successfully employed to fabricate various dental products. For example, CAM production or CAM-milling techniques have been successfully used to fabricate reliable crowns. However, conventional CAD and CAM techniques have failed to efficiently and reliably fabricate dentures. One of the biggest challenges with CAM of dentures has to do with poor fitting of teeth in CAM-milled denture bases. As briefly described above, dentures are chiefly composed of at least two distinct materials—a pink acrylic for the base (e.g., gingiva) and flange portion and a white acrylic (or porcelain) for the teeth. Some dentures can include three or more different materials, depending on a number of layers that make up the teeth. For example, some teeth can be made of at least two layers of acrylic of slightly different colors, and sometimes even three or more layers). Because typical CAM milling "work" blocks of uniform material, the fabricated teeth are limited to single-layer teeth, which can be inferior to two- or higher-layer teeth (e.g., in structural integrity, look, and feel). Consequently, the current state-of-the art in CAM milling of dentures involves milling the gingiva portion, and then gluing third-party manufactured teeth to the CAM-milled gingiva.

However, while CAM-milled gingiva holes (e.g., for receiving or coupling to the teeth) can be fabricated with tolerances on the order of about 10 microns, the dimensions of third-party manufactured teeth can have much larger variations or tolerances, especially due to any polishing and finishing processes that occur after the teeth are pressed. This can make it difficult to accurately fit the teeth in corresponding CAM-milled gingiva holes. Moreover, even if CAM-milled denture teeth can be fabricated to aesthetically compete with multi-layer conventionally fabricated teeth, the milled teeth may still require polishing or processing after milling, which may create similar dimensional variations.

Additionally, to fabricate dental devices using CAD and CAM techniques, it is necessary to obtain a model of a patient's mouth, and to create a design of a denture based on the model. However, conventional techniques of creating a physical model of a patient's mouth can include various steps, such as taking multiple impressions, fabricating models and a custom impression tray, creating a master cast, and determining jaw and occlusal relationships. Because these steps can require multiple patient visits, conventional modeling techniques are unable to leverage the speed and economics of CAD and CAM denture fabrication.

Thus, in various embodiments, the efficiencies of CAD and CAM techniques are leveraged to fabricate dental devices, dentures, and the like, while overcoming one or more of the above-described shortcomings.

In at least one embodiment, a denture form device (e.g., denture form device 600) can be employed to obtain a physical model of a patient's mouth during a CAD and CAM denture fabrication process. More particularly, when a denture form device is inserted and adjusted to fit to a corresponding portion of a patient's mouth (e.g., as described above with respect to FIG. 6), the adjusted denture form device can serve as a physical model of the portion of the patient's mouth, and can provide data including, but not limited to, final impressions anatomy, anatomic landmarks and extensions, vertical dimension, midline, centric relation, smile line, incisal length, interpupillary and ala tragus planes, tooth size, shade, and mold. This model can be provided to a CAD system (e.g., by scanning using a 3-D scanner or the like) for generating a denture model of a corresponding denture. This denture model can then be provided to a CAM system for fabricating an actual denture.

In at least one embodiment, a physical model of a patient's mouth can additionally, or alternatively, be obtained via an intra-oral scan of the mouth. For example, the scan can obtain information on intra-oral cavity, remaining teeth (if any), implants (if any), soft tissue, skeletal devices (e.g., from CT scans), external facial features across a range of facial gestures, jaw movement, and the like. The scanned data can be integrated using software to create a digital model of the patient's mouth that is suitable for creating a denture design that has proper fit, alignment, and occlusion.

In at least one embodiment, an arch device (e.g., arch device 100 or 200) can be combined with CAD and CAM techniques to fabricate a denture. For example, a physical model of a patient's mouth (e.g., obtained by using a denture form device, such as denture form device 1300, or by intra-oral scan of the patient's mouth) can be provided to a system (e.g., a computer system) that has access to a database of digital models (e.g., pre-scanned and pre-stored models) of multiple arch devices.

The system can select an arch device that matches the physical model. For example, the system can select the arch device based on the size of the arch device and the size of the teeth of the arch device. As another example, the system can select the arch device based on tooth shade, photographs of patient's existing teeth, and the like. As yet another example, the system can select the arch device based on general patient information, such as gender, patient preferences, clinician or practitioner preferences, and the like.

In instances where none of the available arch device models is a close match with the physical model, each arch device model can be augmented with a tolerance range (e.g., either by manual input or via one or more digital scans of the corresponding actual arch devices). This additional data for each arch device model can provide information on an amount of adjustment (e.g., in any dimension) that can be made to each arch device, while maintaining the structural and aesthetic integrity of each arch device. In this manner, the system can identify an arch device that most closely matches the physical model. Moreover, the system can also provide adjustment information on how (e.g., in what dimensions and to what degree) the arch device should be adjusted to achieve a proper fit. A dental practitioner (e.g., a clinician) can then select the actual arch device corresponding to the chosen arch device model, and can adjust the arch device based on the adjustment information. In at least one embodiment, the system can also obtain a digital scan of the adjusted arch device to create an adjusted arch device model. The system can further determine if the adjusted arch device will provide a good fit based on the adjusted model. The above process can be repeated until a suitable arch device, with the proper adjustments, is identified.

This model can be provided to a CAD system (e.g., by scanning using a 3-D scanner or the like) for generating a denture model of a corresponding denture. This denture model can then be provided to a CAM system for fabricating an actual denture. After an appropriate arch device is selected and adjusted, a digital model of a CAM-fabricated denture base (e.g., via milling or 3-D printing) can be manipulated in size and orientation (e.g., a channel can be formed in the digital model of the denture base) so as to guide an integration of the arch device to the CAM-fabricated denture base. This can ensure that proper occlusion in the digital model of the denture base is maintained in a final denture.

Since an arch device already includes teeth, it may not be necessary to CAM a gingiva base portion that includes holes for receiving teeth. This can eliminate the above-described problem of teeth variations or tolerances. Rather, a CAM-milled denture base may only be required to include a relatively tolerant surface (e.g., on the order of millimeters, and not microns) for integrating to a base of the arch device, which can be fabricated within any tolerance ranges.

In at least one embodiment, each arch device digital model can be partitioned into two or more model components, which can provide more flexibility in the model comparison or matching process. For example, each model can be partitioned into sub-models, such as a sub-model for an anterior set of teeth, another sub-model for the left posterior set of teeth, and yet another sub-model for the right posterior set of teeth.

Figure 15:
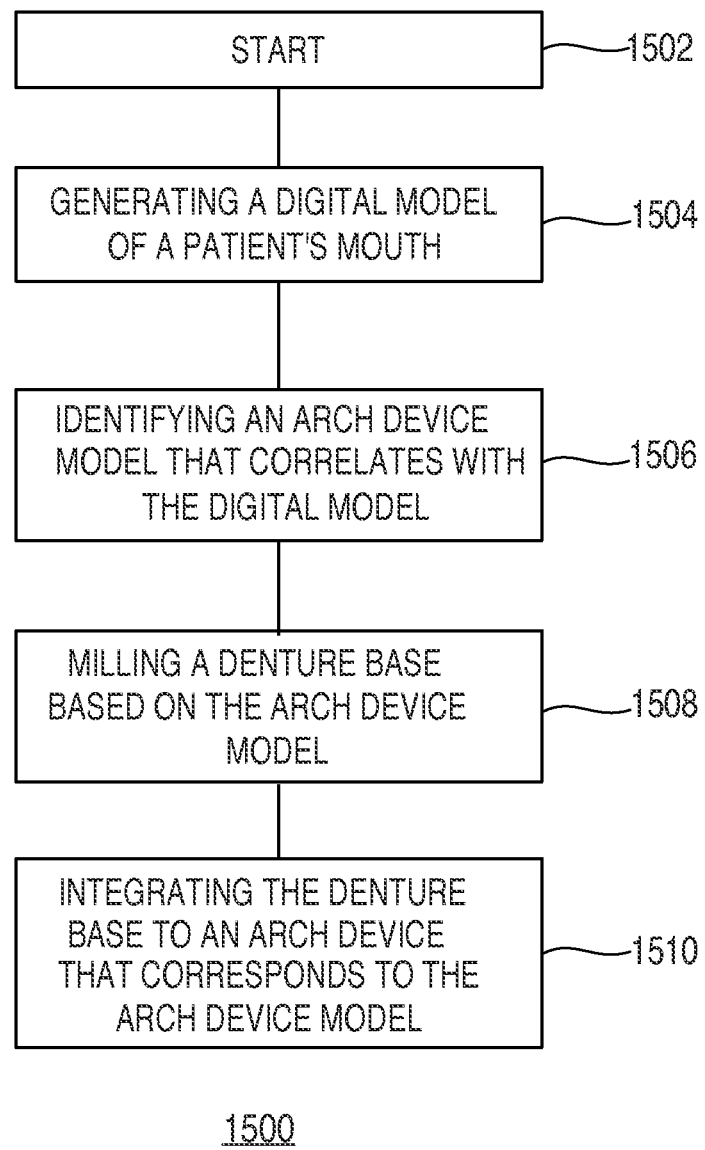
FIG. 15 is an illustrative process for fabricating a denture, in accordance with at least one embodiment.

FIG. 15 is an illustrative process 1500 for fabricating a denture. Process 1500 can begin at step 1502. At step 1504, the process can include generating a digital model of a patient's mouth. For example, the process can include a digital model of a patient's mouth via an intra-oral scan of the mouth. As another example, the process can include generating a digital model of a patient's mouth using a denture form device such as denture form device 600. In this example, the process can include coupling the denture form device to a corresponding portion of the patient's mouth, and adjusting the denture form device until it couples precisely comfortably to the patient's mouth. Alternatively, the process can include adjusting the denture form device prior to coupling to the patient's mouth.

At step 1506, the process can include identifying an arch device model that correlates with the digital model. For example, the process can include identifying an arch device model out of multiple stored arch device models that correlates or is similar to the digital model of the patient's mouth.

At step 1508, the process can include milling a denture base based on the arch device model. For example, the process can include CAM-milling a denture base out of one or more series of milling blocks to form a flange portion of a denture. The flange portion can be milled to integrate with an arch device that corresponds to the arch device model.

At step 1510, the process can include integrating the denture base to an arch device that corresponds to the arch device model. For example, the process can include integrating the CAM-milled denture base to an arch device (e.g., arch device 100 or 200) that corresponds to the identified arch device model that correlates with the digital model of the patient's mouth.

In at least one embodiment, a block device that includes an arch device pre-integrated with denture base material (e.g., flange portion material) is provided. The arch device can be identified (e.g., using the model comparison and matching techniques described above) as being suitable for a patient, and the corresponding block device can be milled to shape a flange portion out of the pre-integrated denture base material to form a denture. In this manner, it may not be necessary to integrate an arch device to a CAM-milled flange portion, since the flange base material is already pre-integrated with the arch device. This can also provide an exact match (e.g., in shade, formulation, etc.) between a base of the arch device and the milled portion of the denture base material.

In at least one embodiment, multi-material or multi-layer milling blocks are provided to form one or more dentures. More particularly, each block can include an arch of tooth-colored material (e.g., acrylic) in one or more layers of varying shades (e.g., to produce multi-layer teeth). The arch of material can be embedded in gingiva-colored material (e.g., acrylic), and can include indentations along a surface to distinguish teeth portions from intra-dental gingiva portions.

In at least one embodiment, a series of multi-material milling blocks is provided to form multiple dentures. The blocks in the series can include arch tooth-colored material of different sizes (e.g., different dimensions of tooth-colored layers), similar to individual arch devices of different sizes, and can be used to form different sized dentures.

Each multi-material block can correspond to a block model that can be scanned and stored in one or more computing components of a system. These models can be accessed during a denture fabrication process to identify a suitable milling block based on a model of a patient's mouth.

Figure 16:
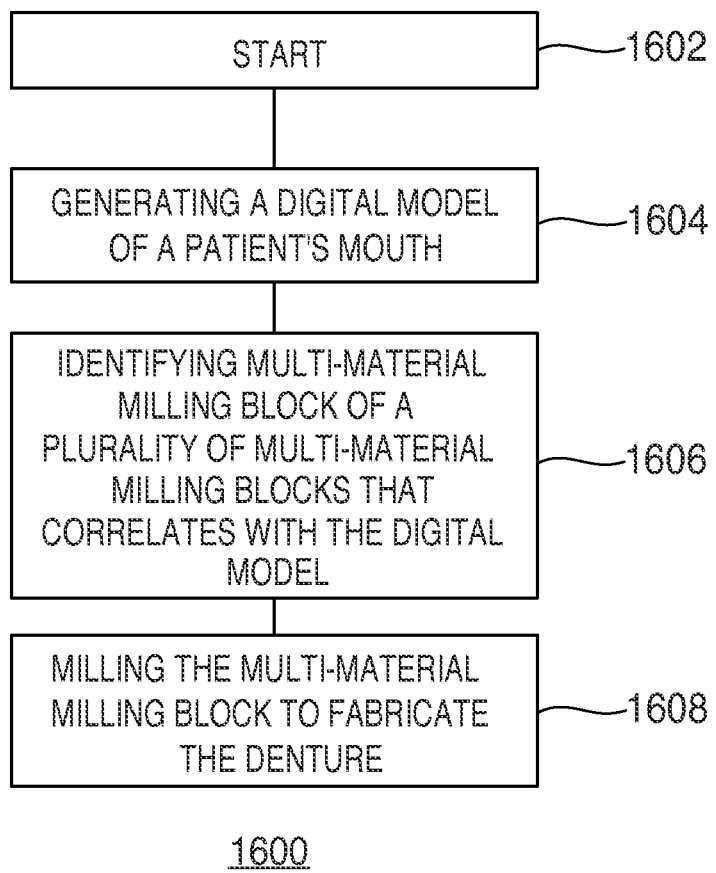
FIG. 16 is another illustrative process for fabricating a denture, in accordance with at least one embodiment.

FIG. 16 is another illustrative process 1600 for fabricating a denture. Process 1600 can begin at step 1602. At step 1604, the process can include generating a digital model of a patient's mouth. For example, the process can include generating a digital model of a patient's mouth via an intra-oral scan of the mouth. As another example, the process can include generating a digital model of a patient's mouth using a denture form device such as denture form device 600.

At step 1606, the process can include identifying multi-material milling block of a plurality of multi-material milling blocks that correlates with the digital model. For example, the process can include identifying a multi-material milling block of multiple multi-material milling blocks by accessing pre-stored computer models of the milling blocks. Any one of the models that correlates or closely matches the digital model of the patient's mouth can be selected.

At step 1608, the process can include milling the multi-material milling block to fabricate the denture. For example, the process can include CAM-milling the identified multi-material milling block to fabricate a denture that corresponds to the patient's mouth.

In at least one embodiment, a denture can be fabricated via a CAM-milling technique similar to conventional CAM-milling (e.g., where a flange portion of a denture is milled with gingiva holes for coupling to third-party manufactured teeth). However, rather than milling gingiva holes (e.g., the holes on the base portion of the denture for receiving or coupling to the teeth) to have sizes that exactly correspond to the sizes of the corresponding teeth (e.g., as in conventional CAM-milling), the gingiva holes can instead be fabricated with varying tolerances along their depths. More particularly, an interior anatomy at the root of a tooth can have a large tolerance relative to that of an occlusal anatomy of the tooth (e.g., the labial and lingual surfaces that meet other teeth). Thus, the gingiva holes can be milled with larger tolerances deeper into the holes that support the teeth. In this manner, the larger tolerances at the lower ends of the holes can accommodate larger tolerances of the roots of the corresponding teeth.

In at least one embodiment, a denture can be fabricated using 3-D printing techniques. For example, rather than integrating an identified arch device (e.g., using the model comparison technique described above) with a CAM-milled flange, the identified arch device can be integrated with a 3-D printed flange. As another example, rather than milling a gingiva portion with holes that have varying tolerances along their depths (e.g., as described above), a gingiva portion can be 3-D printed with holes having such varying tolerances.

Although various CAD, CAM, and 3-D printing fabrication techniques have been described above with respect to fabricating full dentures, it should be appreciated that similar techniques can be provided and employed to fabricate partial dentures.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is understood that one or more features of an embodiment can be combined with one or more features of another embodiment to provide systems and/or methods without deviating from the spirit and scope of the invention.

Additionally, it is to be understood that the steps of each of processes 800, 900, 1000, 1100, 1500, and 1600 are merely illustrative and that the steps can be modified, added, or omitted.

Moreover, the previously described embodiments are presented for purposes of illustration and not of limitation. Those skilled in the art will appreciate that the invention can be practiced by other than the described embodiments, and the invention is limited only by the claims which follow.

What is claimed is:

1. An arch device for a permanent denture, the denture comprising a flange portion coupled to the base of the arch device, the arch device comprising:
   an arch-shaped base comprising a material that is malleable and can be adjusted at temperatures between approximately 130 degrees Fahrenheit and 212 degrees Fahrenheit, wherein the base:
      has a flat, smooth surface that is free of any holes or dimples that would interface with implants embedded in a patient's gums; and
      lacks a flange; and
   a plurality of teeth positioned along the base and coupled to the base, wherein the plurality of teeth comprises a rigid acrylic material that is not malleable at temperatures between 130 degrees Fahrenheit and 212 degrees Fahrenheit.

2. The arch device of claim 1, wherein:
   the base is at least partially comprised of polymer and monomer; and
   at least one of the polymer and the monomer is plasticized.

3. The arch device of claim 2, wherein a ratio of the polymer to the monomer is approximately 63.5% to 36.5% by weight.

4. The arch device of claim 1, wherein the base comprises a material that can be further adjustable when reheated to temperatures between approximately 130 degrees Fahrenheit and approximately 212 degrees Fahrenheit after becoming rigid by being subjected to temperatures below 130 degrees Fahrenheit.

5. A denture form device comprising:
   a unitary structure having a base portion and a flange portion, the structure comprising a polymer and a monomer mixed in a predefined ratio such that the entire structure is adjustable when subjected to heat, and at least one of the polymer and the monomer being plasticized;
   a plurality of teeth integrated with the base portion; and
   a distinct extension portion integrated to the base portion, the extension portion being at least partially comprised of additional denture base material, wherein the distinct extension portion allows a width of the denture form device to be adjusted when subjected to heat.

6. The denture form device of claim 5, wherein when the denture form device is subjected to heat, the denture form device being subjected to warm fluid.

7. The denture form device of claim 5, wherein the heat corresponds to a temperature of about 175 degrees Fahrenheit.

8. The denture form device of claim 5, wherein the predetermined ratio of the polymer to the monomer allows at least one of the base portion, the distinct extension portion, and at least one tooth of the plurality of teeth to be adjusted to receive at least one of:
  impressions of a patient's mouth; and
  measurements useful for denture fabrication after the denture form device is subjected to heat.

9. A denture comprising:
  an arch device comprising:
    a lingual portion, wherein the lingual portion is an arch-shaped base comprising a material that is malleable and can be adjusted at temperatures between approximately 130 degrees Fahrenheit and 212 degrees Fahrenheit, wherein the base:
      has a flat, smooth surface that is free of any holes or dimples that would interface with implant's embedded in a patient's gums; and
    a plurality of teeth positioned along the base and coupled to the base, wherein the plurality of teeth comprises a rigid acrylic material that is not malleable at temperatures between 130 degrees Fahrenheit and 212 degrees Fahrenheit; and
  a flange coupled to the arch device, wherein the flange comprises a material that is not malleable at temperatures between 130 degrees Fahrenheit and 212 degrees Fahrenheit in order to maintain the structural integrity of the denture, and wherein the flange extends from the lingual section to a border of the denture.

* * * * *